United States Patent
Omura et al.

(10) Patent No.: US 10,202,627 B2
(45) Date of Patent: Feb. 12, 2019

(54) METHOD FOR PRODUCING TREHANGELIN

(71) Applicants: THE KITASATO INSTITUTE, Tokyo (JP); NAGASE & CO., LTD., Osaka-shi, Osaka (JP)

(72) Inventors: Satoshi Omura, Tokyo (JP); Yoko Takahashi, Tokyo (JP); Takuji Nakashima, Tokyo (JP); Yuki Inahashi, Tokyo (JP)

(73) Assignees: The Kitasato Institute, Tokyo (JP); Nagase & Co., Ltd., Osaka-shi, Osaka (JP)

(*) Notice: Subject to any disclaimer, the term of this patent is extended or adjusted under 35 U.S.C. 154(b) by 0 days.

(21) Appl. No.: 15/444,914

(22) Filed: Feb. 28, 2017

(65) Prior Publication Data

US 2017/0306371 A1 Oct. 26, 2017

(30) Foreign Application Priority Data

Mar. 4, 2016 (JP) ................. 2016-042045

(51) Int. Cl.
| | | |
|---|---|---|
| *C12N 15/00* | (2006.01) | |
| *C12P 19/12* | (2006.01) | |
| *C12N 9/04* | (2006.01) | |
| *C12N 9/10* | (2006.01) | |
| *C12N 9/88* | (2006.01) | |
| *C12N 15/52* | (2006.01) | |

(52) U.S. Cl.
CPC ............. *C12P 19/12* (2013.01); *C12N 9/0006* (2013.01); *C12N 9/1025* (2013.01); *C12N 9/1029* (2013.01); *C12N 9/88* (2013.01); *C12N 15/52* (2013.01); *C12Y 101/0133* (2015.07); *C12Y 203/01199* (2015.07); *C12Y 402/01017* (2013.01)

(58) Field of Classification Search
CPC ...... C12N 9/0006; C12N 9/1205; C12N 9/88; C12N 15/86; A61K 38/00

USPC .................. 435/189, 194, 232, 252.3, 320.1; 536/23.2
See application file for complete search history.

(56) References Cited

FOREIGN PATENT DOCUMENTS

| JP | 2015-024985 A | 2/2015 |
|---|---|---|
| WO | WO 2014/034147 A1 | 6/2014 |

OTHER PUBLICATIONS

The 2012 Annual Meeting of the Society for Actinomycetes Japan Abstracts, Fuchu, Tokyo, Sep. 6-7, 2012.
The 2015 Annual Meeting of the Society for Actinomycetes Japan Book of Abstracts.
136th Annual Meeting of the Pharmaceutical Society of Japan, 2016, Study on anti-aging effects of trehangelin, a new trehalose compound (Abstract only).
Inahashi et al., "Biosynthesis of Trehangelin in *Polymorphospora rubra* K07-0510: Identification of Metabolic Pathway to Angelyl-CoA," *ChemBioChem*, vol. 17, pp. 1442-1447 (2016).
Nakashima et al., "Trehangelins A, B and C, novel photo-oxidative hemolysis inhibitors produced by an endophytic actinomycete, *Polymorphospora rubra* K07-0510," *The Journal of Antibiotics*, pp. 1-7 (2013).

*Primary Examiner* — Tekchand Saidha
(74) *Attorney, Agent, or Firm* — Knobbe, Martens, Olson & Bear, LLP

(57) ABSTRACT

An object of the present invention is to provide enzymes and a DNA encoding the enzymes that are involved in biosynthesis of trehangelin which has the potential to be a therapeutic agent for photosensitivity disorder and cosmetics, and to provide a method for producing trehangelin by utilizing the enzymes and a recombinant microorganism. The present invention is directed to a protein having an amino acid sequence of SEQ ID NO: 3, 5, 7 or 9, or a protein having an amino acid sequence of SEQ ID NO: 3, 5, 7 or 9 in which one to several amino acids are deleted, substituted, added and/or inserted or an amino acid sequence having 60% or more homology with the amino acid sequence of SEQ ID NO: 3, 5, 7 or 9 and having an enzyme activity involved in biosynthesis of trehangelin; and a DNA encoding said protein.

10 Claims, 2 Drawing Sheets
Specification includes a Sequence Listing.

METHOD FOR PRODUCING TREHANGELIN

CROSS-REFERENCE TO RELATED APPLICATIONS

All documents cited herein are entirely incorporated herein by reference. The present application claims priority to Japanese Patent Application No. 2016-042045 filed on 4 Mar. 2016, which is entirely incorporated herein by reference.

BACKGROUND OF THE INVENTION

Field of the Invention

The present invention relates to the field of trehangelin synthesis.

Description of the Related Art

Trehangelin A, trehangelin B and trehangelin C has been discovered from secondary metabolites of an actinomycete *Polymorphospora rubra* K07-0510 isolated from the roots of an Orchidaceae plant. Trehangelins are compounds in which 1 trehalose molecule and 2 angelic acid molecules are condensed, and have an effect of suppressing light-induced cytotoxicity of pheophorbide a, i.e. a cryoprotection effect. Trehangelin A and trehangelin B do not exhibit toxicity towards animal cells (particularly, human cells), and are safe substances. Further, the trehangelins do not exhibit antimicrobial activity towards Gram-negative bacteria, Gram-positive bacteria and fungi, and are believed to have no effect on indigenous bacteria upon use thereof on human bodies (Japanese Patent Laid-Open No. 2015-024985).

As described above, trehangelins are safe and useful substances and are expected to be applied to medicaments such as therapeutic agents for photosensitivity disorder and cosmetics. Establishment of an inexpensive production method of trehangelin may be of great benefit in the medical field. It is difficult to allow condensation of angelic acid to the arbitrary hydroxy group of trehalose by organic chemistry, and thus synthesis of trehangelin is difficult without an enzyme reaction. However, the synthesis system of trehangelin which may be present in *Polymorphospora rubra* K07-0510 has not been identified.

SUMMARY OF THE INVENTION

The present invention is aimed to provide enzymes and a DNA sequence encoding the enzymes that is involved in biosynthesis of trehangelin, the potential compound as a therapeutic agent for photosensitivity disorder and cosmetics. Further, the present invention is aimed to provide a method for producing trehangelin by utilizing the enzymes and a microorganism recombined with the DNA having the sequence.

The inventors of the present invention sought to obtain DNAs encoding enzymes involved in trehangelin synthesis in an actinomycete *Polymorphospora rubra* K07-0510, i.e. a gene encoding 3-ketoacyl-CoA synthase, a gene encoding 3-ketoacyl-CoA reductase, a gene encoding enoyl-CoA hydratase and a gene encoding acyltransferase, examined whether or not a transformant obtained by cloning of the above 4 genes could produce trehangelin, and analysed expression and function of the enzymes in the transformant having the genes encoding the enzymes, thereby completing the present invention. In this way, the inventors of the present invention found novel enzymes involved in biosynthesis of trehangelin from an actinomycete *Polymorphospora rubra* K07-0510 to complete the present invention.

Thus, the present invention relates to:
(1) A nucleic acid molecule having at least one base sequence selected from following (i) to (iv):
  (i) a base sequence of SEQ ID NO: 2, or
  a base sequence encoding an amino acid sequence of SEQ ID NO: 3, or
  a base sequence encoding an amino acid sequence of SEQ ID NO: 3 in which one to several amino acids are deleted, substituted, added and/or inserted, or a base sequence having 90% or more identity with the base sequence of SEQ ID NO: 2, wherein a protein encoded by the base sequence has 3-ketoacyl-CoA synthase activity;
  (ii) a base sequence of SEQ ID NO: 4, or
  a base sequence encoding an amino acid sequence of SEQ ID NO: 5, or
  a base sequence encoding an amino acid sequence of SEQ ID NO: 5 in which one to several amino acids are deleted, substituted, added and/or inserted, or a base sequence having 90% or more identity with the base sequence of SEQ ID NO: 4, wherein a protein encoded by the base sequence has a 3-ketoacyl-CoA reductase activity;
  (iii) a base sequence of SEQ ID NO: 6, or
  a base sequence encoding an amino acid sequence of SEQ ID NO: 7, or
  a base sequence encoding an amino acid sequence of SEQ ID NO: 7 in which one to several amino acids are deleted, substituted, added and/or inserted, or a base sequence having 90% or more identity with the base sequence of SEQ ID NO: 6, wherein a protein encoded by the base sequence has an enoyl-CoA hydratase activity; and
  (iv) a base sequence of SEQ ID NO: 8, or
  a base sequence encoding an amino acid sequence of SEQ ID NO: 9, or
  a base sequence encoding an amino acid sequence of SEQ ID NO: 9 in which one to several amino acids are deleted, substituted, added and/or inserted, or a base sequence having 90% or more identity with the base sequence of SEQ ID NO: 8, wherein a protein encoded by the base sequence has an acyltransferase activity.
(2) The nucleic acid molecule of (1), comprising all of the base sequences of (i) to (iv) as recited in (1).
(3) The nucleic acid molecule of (2), which is a nucleic acid molecule having
  a base sequence of SEQ ID NO: 1, or
  a base sequence encoding an amino acid sequence encoded by the base sequence of SEQ ID NO: 1 in which one to several amino acids are deleted, substituted, added and/or inserted, or
  a base sequence having 90% or more identity with the base sequence of SEQ ID NO: 1.
(4) The nucleic acid molecule of (1), which is
  a nucleic acid molecule having a base sequence of SEQ ID NO: 2, or
  a nucleic acid molecule having a base sequence encoding an amino acid sequence of SEQ ID NO: 3, or
  a nucleic acid molecule having a base sequence encoding an amino acid sequence of SEQ ID NO: 3 in which one to several amino acids are deleted, substituted, added and/or inserted or a base sequence having 90% or more identity with the base sequence of SEQ ID NO: 2, wherein a protein encoded by the base sequence has a 3-ketoacyl-CoA synthase activity.

(5) The nucleic acid molecule of (1), which is
a nucleic acid molecule having a base sequence of SEQ ID NO: 4, or
a nucleic acid molecule having a base sequence encoding an amino acid sequence of SEQ ID NO: 5, or
a nucleic acid molecule having a base sequence encoding an amino acid sequence of SEQ ID NO: 5 in which one to several amino acids are deleted, substituted, added and/or inserted, or a base sequence having 90% or more identity with the base sequence of SEQ ID NO: 4, wherein a protein encoded by the base sequence has a 3-ketoacyl-CoA reductase activity.
(6) The nucleic acid molecule of (1), which is
a nucleic acid molecule having a base sequence of SEQ ID NO: 6, or
a nucleic acid molecule having a base sequence encoding an amino acid sequence of SEQ ID NO: 7, or a nucleic acid molecule having a base sequence encoding an amino acid sequence of SEQ ID NO: 7 in which one to several amino acids are deleted, substituted, added and/or inserted, or a base sequence having 90% or more identity with the base sequence of SEQ ID NO: 6, wherein a protein encoded by the base sequence has an enoyl-CoA hydratase activity.
(7) The nucleic acid molecule of (1), which is
a nucleic acid molecule having a base sequence of SEQ ID NO: 8,
a nucleic acid molecule having a base sequence encoding an amino acid sequence of SEQ ID NO: 9, or
a nucleic acid molecule having a base sequence encoding an amino acid sequence of SEQ ID NO: 9 in which one to several amino acids are deleted, substituted, added and/or inserted, or a base sequence having 90% or more identity with the base sequence of SEQ ID NO: 8, wherein a protein encoded by the base sequence has an acyltransferase activity.
(8) A protein having an amino acid sequence of SEQ ID NO: 3, or
a protein having an amino acid sequence of SEQ ID NO: 3 in which one to several amino acids are deleted, substituted, added and/or inserted or an amino acid sequence having 60% or more homology with the amino acid sequence of SEQ ID NO: 3, and having a 3-ketoacyl-CoA synthase activity.
(9) A protein having an amino acid sequence of SEQ ID NO: 5, or
a protein having an amino acid sequence of SEQ ID NO: 5 in which one to several amino acids are deleted, substituted, added and/or inserted or an amino acid sequence having 60% or more homology with the amino acid sequence of SEQ ID NO: 5, and having a 3-ketoacyl-CoA reductase activity.
(10) A protein having an amino acid sequence of SEQ ID NO: 7, or
a protein having an amino acid sequence of SEQ ID NO: 7 in which one to several amino acids are deleted, substituted, added and/or inserted or an amino acid sequence having 60% or more homology with the amino acid sequence of SEQ ID NO: 7, and having an enoyl-CoA hydratase activity.
(11) A protein having an amino acid sequence of SEQ ID NO: 9, or
a protein having an amino acid sequence of SEQ ID NO: 9 in which one to several amino acids are deleted, substituted, added and/or inserted or an amino acid sequence having 60% or more homology with the amino acid sequence of SEQ ID NO: 9, and having an acyltransferase activity.
(12) A vector comprising the nucleic acid molecule of any one of (1) to (7).
(13) A transformant comprising the vector of (12).
(14) The transformant of (13), which is *Escherichia coli*.
(15) A method for producing trehangelin comprising culturing the transformant of (13) or (14) to produce trehangelin.
(16) A method for producing trehangelin at least comprising reacting a protein of any one of (8) to (11) with a substrate.
(17) The method for producing trehangelin of (16), comprising reacting all of the proteins of (8) to (11) with a substrate.

In one aspect, the present invention relates to enzymes involved in trehangelin synthesis and a nucleic acid molecule encoding the enzymes. The term "trehangelin" as used herein means the compound represented by the following general formula:

[Formula 1]

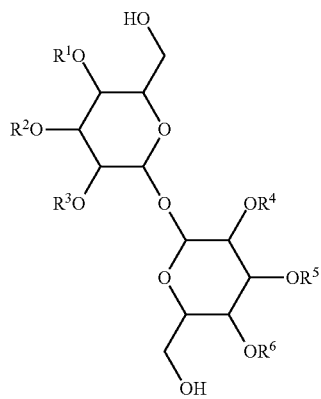

[wherein, any one of R1 to R3 is a 2-methylbut-2-enoyl group and remaining two of R1 to R3 represent hydrogen atoms; and any one of R4 to R6 is a 2-methylbut-2-enoyl group and remaining two of R4 to R6 represent hydrogen atoms.]

Examples of trehangelins as used herein include trehangelin A, trehangelin B and trehangelin C. Trehangelin A is a compound represented by the following formula I:

[Formula 2]

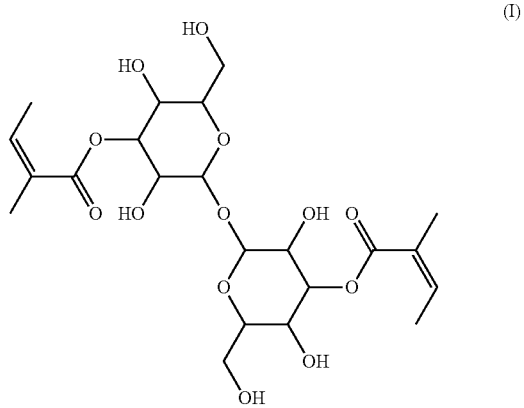

trehangelin A

Trehangelin B as used herein is a compound represented by the following formula II:

[Formula 3]

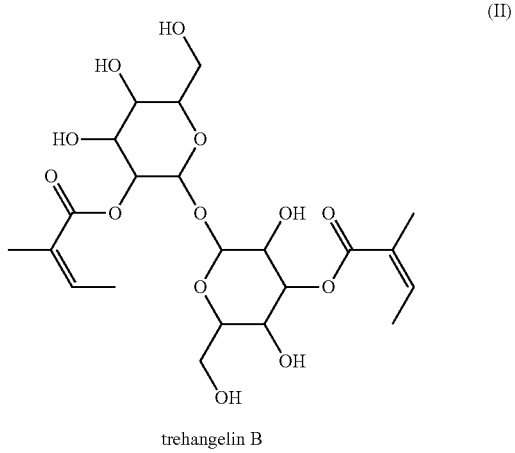

trehangelin B

Trehangelin C as used herein is a compound represented by the following formula III:

[Formula 4]

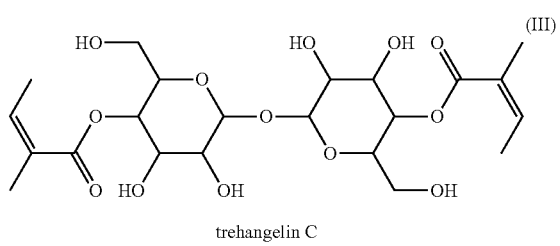

trehangelin C

The "trehangelin synthesis" as used herein means at least one step selected from the following (a) to (d). In other words, trehangelin synthesis comprises one or more (2, 3 or all) steps selected from the following (a) to (d):
(a) reacting acetyl-CoA with methylmalonyl-CoA to produce 2-methylacetoacetyl-CoA;
(b) converting 2-methylacetoacetyl-CoA into 3-hydroxy-2-methylbutyryl-CoA;
(c) converting 3-hydroxy-2-methylbutyryl-CoA into angelyl-CoA; and
(d) reacting angelyl-CoA with trehalose to produce trehangelin.

Therefore, the present invention encompasses one or more (2, 3 or all) methods selected from the following (a) to (d):
(a) a method for reacting acetyl-CoA with methylmalonyl-CoA to produce 2-methylacetoacetyl-CoA;
(b) a method for converting 2-methylacetoacetyl-CoA to 3-hydroxy-2-methylbutyryl-CoA;
(c) a method for converting 3-hydroxy-2-methylbutyryl-CoA to angelyl-CoA; and
(d) a method for reacting angelyl-CoA with trehalose to produce trehangelin.

The "enzymes involved in trehangelin synthesis" as used herein means enzymes catalysing the above steps (a) to (d), and specifically means 3-ketoacyl-CoA synthase (catalysing the step (a)), 3-ketoacyl-CoA reductase (catalysing the step (b)), enoyl-CoA hydratase (catalysing the step (c)), and acyltransferase (catalysing the step (d)).

The enzymes involved in trehangelin synthesis as used herein typically are proteins having amino acid sequences of SEQ ID NO: 3 (3-ketoacyl-CoA synthase), SEQ ID NO: 5 (3-ketoacyl-CoA reductase), SEQ ID NO: 7 (enoyl-CoA hydratase), and SEQ ID NO: 9 (acyltransferase). The enzymes, as used herein, may be proteins having amino acid sequences of SEQ ID NO: 3 (3-ketoacyl-CoA synthase), SEQ ID NO: 5 (3-ketoacyl-CoA reductase), SEQ ID NO: 7 (enoyl-CoA hydratase) or SEQ ID NO: 9 (acyltransferase) in which one to several amino acids are deleted, substituted, added and/or inserted. The phrase "one to several amino acids are deleted, substituted, added and/or inserted" as used herein means any number of amino acids, for example 1 to 20, preferably 1 to 15, more preferably 1 to 10 and still more preferably 1 to 5 are deleted, substituted, added and/or inserted. In addition, the enzymes, as used herein, may be proteins having 60% or more homology or identity or, for example, 70% or more, 80% or more, 85% or more, 90% or more, 95% or more, 96% or more, 97% or more, 98% or more or 99% or more homology or identity with amino acid sequences of SEQ ID NO: 3 (3-ketoacyl-CoA synthase), SEQ ID NO: 5 (3-ketoacyl-CoA reductase), SEQ ID NO: 7 (enoyl-CoA hydratase) and SEQ ID NO: 9 (acyltransferase). The homology or identity of amino acid sequences may be examined by using a tool well known in the art such as BLAST (Basic Local Alignment Search Tool).

As used herein, a "protein having an amino acid sequence in which one to several amino acids are deleted, substituted, added and/or inserted" and a "protein having an amino acid sequence that has 60% or more (and the like) homology" have the same biological activity, i.e. an enzyme activity, of the protein having the original amino acid sequence. The biological activities of these proteins need to have the same nature but are not necessary to have the same degree of activities as that of the protein having the original amino acid sequence. Specifically, a protein having an amino acid sequence of SEQ ID NO: 3 in which one to several amino acids are deleted, substituted, added and/or inserted and a protein having 60% or more (and the like) homology or identity with the amino acid sequence of SEQ ID NO: 3 have a 3-ketoacyl-CoA synthase activity that catalyses the above reaction (a). A protein having an amino acid sequence of SEQ ID NO: 5 in which one to several amino acids are deleted, substituted, added and/or inserted and a protein having a 60% or more or the like homology or identity with the amino acid sequence of SEQ ID NO: 5 have a 3-ketoacyl-CoA reductase activity that catalyses the above reaction (b). A protein having an amino acid sequence of SEQ ID NO: 7 in which one to several amino acids are deleted, substituted, added and/or inserted and a protein having 60% or more (and the like) homology or identity with the amino acid sequence of SEQ ID NO: 7 have an enoyl-CoA hydratase activity that catalyses the above reaction (c). A protein having an amino acid sequence of SEQ ID NO: 9 in which one to several amino acids are deleted, substituted, added and/or inserted and a protein having 60% or more (and the like) homology or identity with the amino acid sequence of SEQ ID NO: 9 have an acyltransferase activity catalysing the above reaction (d). Throughout herein, whether or not a protein has a desired enzyme activity can be confirmed by reacting the protein with a corresponding substrate under the condition that the original protein can catalyse, and by detecting an expected product to be obtained. When even a small amount of the expected product is detected, the protein can be determined to have the enzyme activity.

In another aspect, the present invention relates to a nucleic acid molecule having a base sequence encoding any of the above enzymes. As an specific example, the nucleic acid molecule of the present invention is a nucleic acid molecule having at least one base sequence selected from base sequences of SEQ ID NO: 2, SEQ ID NO: 4, SEQ ID NO: 6 and SEQ ID NO: 8. The nucleic acid molecule of the present invention further encompasses a base sequence having 90% or more identity with the base sequence of SEQ ID NO: 2, a base sequence having 90% or more identity with the base sequence of SEQ ID NO: 4, a base sequence having 90% or more identity with the base sequence of SEQ ID NO: 6 and a base sequence having 90% or more identity with the base sequence of SEQ ID NO: 8. The identity can exceed 90% or more, for example 95% or more, 96% or more, 97% or more, 98% or more or 99% or more. The identity of nucleic acid sequences may be examined by using a tool well known in the art such as BLAST (Basic Local Alignment Search Tool).

As used herein, "a nucleic acid molecule having a base sequence that has 90% or more (and the like) identity" encodes a protein having a biological activity of the protein encoded by the original nucleic acid molecule, namely an enzyme activity. Thus, for example, a protein encoded by a base sequence that has 90% or more identity with the base sequence of SEQ ID NO: 2 has a 3-ketoacyl-CoA synthase activity that catalyses the above reaction (a). Similarly, a protein encoded by a base sequence that has 90% or more identity with the base sequence of SEQ ID NO: 4 has a 3-ketoacyl-CoA reductase activity catalysing the above reaction (b). A protein encoded by a base sequence that has 90% or more identity with the base sequence of SEQ ID NO: 6 has an enoyl-CoA hydratase activity catalysing the above reaction (c). A protein encoded by a base sequence that has 90% or more identity with the base sequence of SEQ ID NO: 8 has an acyltransferase activity catalysing the above reaction (d).

It is sufficient that the nucleic acid molecule of the present invention may have a base sequence encoding at least one enzyme selected from the above described enzymes, alternatively, the nucleic acid molecule may have a base sequence encoding two or more (for example, 2, 3 or all) enzymes. When the nucleic acid molecule of the present invention has a base sequence encoding two or more enzymes, each of base sequences encoding the respective enzymes may be linked via any non-coding region that does not have the initiation codon. Alternatively, when the nucleic acid molecule of the present invention has a base sequence encoding two or more enzymes, the base sequences may encode the enzymes with partial overlap. For example, the base sequence of SEQ ID NO: 1 has all base sequences of SEQ ID NO: 2, SEQ ID NO: 4, SEQ ID NO: 6 and SEQ ID NO: 8, and the positions 1 to 828 of SEQ ID NO: 1 correspond to the base sequence of SEQ ID NO: 2, the positions 875 to 1900 of SEQ ID NO: 1 correspond to the base sequence of SEQ ID NO: 4, the positions 1905 to 2684 of SEQ ID NO: 1 correspond to the base sequence of SEQ ID NO: 6, and the positions 2681 to 3475 of SEQ ID NO: 1 correspond to the base sequence of SEQ ID NO: 8. In SEQ ID NO: 1, non-coding regions exist between SEQ ID NO: 2 and SEQ ID NO: 4, and between SEQ ID NO: 4 and SEQ ID NO: 6. SEQ ID NO: 6 and SEQ ID NO: 8 partly share the nucleic acid sequence as an overlapping coding region in SEQ ID NO: 1.

As used herein, the "nucleic acid molecule" means DNA, RNA or a mixture of DNA and RNA. The nucleic acid molecule may be modified as far as the molecule can express a desired protein. The present invention also encompasses a nucleic acid molecule having a base sequence that is complementary to a base sequence encoding at least one enzyme selected from the above enzymes.

According to another aspect of the invention, a vector containing a DNA and/or RNA that has a base sequence encoding the enzymes is provided. The vector of the present invention is not particularly limited as far as the vector can express the DNA and/or RNA in a microorganism, and is preferably able to replicate or to be integrated into a chromosome in a host, *Escherichia coli* or an actinomycete. The vector of the present invention may contain, in addition to the above DNA and/or RNA, a terminator sequence, a promoter region, a ribosome binding sequence and/or a promoter controlling sequence. The vector of the present invention preferably contains a promoter region, and in this case, the promoter preferably locates at a position that allows the promoter to control expression of the DNA and/or RNA. The vector may be either of a phage vector and a plasmid vector, and is preferably a vector expressed in *E. coli* or an actinomycete. Examples of the vector of the present invention include ZAP Express [produced by Stratagene Corp., Strategies, 5, 58 (1992)], pBluescript II SK(+) [Nucleic Acids Research, 17, 9494 (1989)], Lambda ZAP II (produced by Stratagene Corp.), lambda gt10, lambda gt11 [DNA Cloning, A Practical Approach, 1, 49 (1985)], lambda TriplEx (produced by Clonetech Laboratories, Inc.), lambda ExCell (produced by Pharmacia Corp.), pT7T318U (produced by Pharmacia Corp.), pcD2 [Mol. Gen. Biol., 3, 280 (1983)], pMW218 (produced by Wako Pure Chemical Industries Ltd.), UC118 (produced by Takara Shuzo Co., Ltd.), pEG400 [J. Bac., 172, 2392 (1990)], pQE-30 (produced by Qiagen), pBTrp2, pBTac1, pBTac2 (all marketed by Boehringer Mannheim), pKK233-2 (produced by Pharmacia Corp.), pSE280 (produced by Invitrogen), pGEMEX-1 (produced by Promega Corporation), pQE-8 (produced by Qiagen), pQE-30 (produced by Qiagen), pKYP200 [Agricultural Biological Chemistry, 48, 669 (1984)], pLSA1 [Agricultural Biological Chemistry., 53, 277 (1989)], pGEL1 [Proc. Natl. Acad. Sci. USA, 82, 4306 (1985)], pBluescript II SK+, pBluescript II SK− (produced by Stratagene Corp.), pTrS30 (FERMBP-5407), pTrS32 (FERMBP-5408), pGEX (produced by Pharmacia Corp.), pET-3 (produced by Novagen), pET-15b (produced by Novagen), pSupex, pUB110, pTP5, pC194, pUC18 [Gene, 33, 103 (1985)], pUC19 [Gene, 33, 103 (1985)], pSTV28 (produced by Takara Shuzo Co., Ltd.), pSTV29 (produced by Takara Shuzo Co., Ltd.), pUC118 (produced by Takara Shuzo Co., Ltd.), pCold I (produced by Takara Shuzo Co., Ltd.), pEG400 [J. Bacteriol., 172, 2392 (1990)] and the like.

Any promoter can be used as long as that can express in a host, an actinomycete cell. Examples of the promoter include promoters derived from *E. coli* and phages such as the trp promoter (Ptrp), the lac promoter (Plac), the PL promoter, the PR promoter and the PSE promoter; the SP01 promoter; the SP02 promoter; the penP promoter and the like. Artificially designed and modified promoters such as the promoter including two Ptrps in series (Prp×2), the tac promoter, the letI promoter and the lacT7 promoter may also be used.

Any ribosome binding sequence can be used as long as that can be expressed in a host, an actinomycete cell. It is preferable to use a vector in which the distance between the Shine-Dalgarno sequence and the initiation codon is appropriately adjusted (for example, 6 to 18 bases).

According to another aspect of the present invention, a transformant or host cell containing the above vector is provided. Examples of the transformant or host cell include microorganisms belonging to the following genera: *Escherichia, Corynebacterium, Brevibacterium, Bacillus, Microbacterium, Serratia, Pseudomonas, Agrobacterium, Alicyclobacillus, Anabaena, Anacystis, Arthrobacter, Azobacter, Chromatium, Erwinia, Methylobacterium, Phormidium, Rhodobacter, Rhodopseudomonas, Rhodospirillum, Scenedesmun, Streptomyces, Synnecoccus, Zymomonas* and the like. Preferably microorganisms belonging to the following genera may be mentioned: *Escherichia, Corynebacterium, Brevibacterium, Bacillus, Pseudomonas, Agrobacterium, Alicyclobacillus, Anabaena, Anacystis, Arthrobacter, Azobacter, Chromatium, Erwinia, Methylobacterium, Phormidium, Rhodobacter, Rhodopseudomonas, Rhodospirillum, Scenedesmun, Streptomyces, Synnecoccus, Zymomonas* and the like. Examples of the actinomycete include *Streptomyces albus, Streptomyces lividans, Streptomyces chromofuscus, Streptomyces exfoliatus* and *Streptomyces argenteorus*. The transformant of the present invention may be any host cell as far as that is capable of efficiently expressing the enzyme protein, and is preferably *E. coli*, baker's yeast or an actinomycete (genus *Streptomyces*), more preferably *E. coli* or an actinomycete, and the most preferably *E. coli*.

Figure 1:
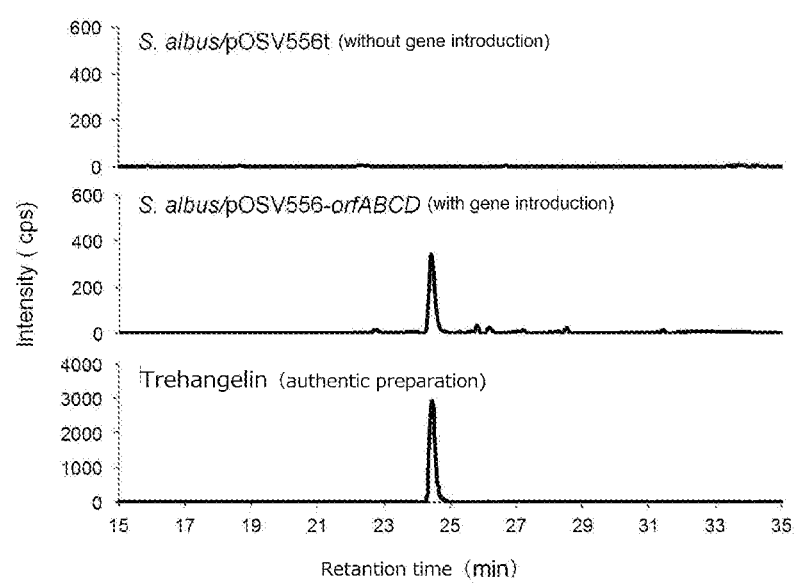
FIG. 1 shows the result of detection of trehangelin production from an actinomycete transformed with orfA, orfB, orfC and orfD by LC/MS.

DETAILED DESCRIPTION OF THE PREFERRED EMBODIMENTS (1) Obtaining Nucleic Acid Molecules The nucleic acid molecule of the present invention may be obtained by PCR. For example, a nucleic acid molecule (for example, DNA) having a base sequence of SEQ ID NO: 1, SEQ ID NO: 2, SEQ ID NO: 4, SEQ ID NO: 6 or SEQ ID NO: 8 may be obtained by carrying out PCR, in which the chromosomal DNA of an actinomycete *Polymorphospora rubra* K07-0510 is used as a template with a pair of primers designed to allow amplification of the base sequence of SEQ ID NO: 1, SEQ ID NO: 2, SEQ ID NO: 4, SEQ ID NO: 6 or SEQ ID NO: 8, utilizing Expand™ High Fidelity PCR System (produced by Roche Life Science) and the like on a DNA Thermal Cycler (produced by Applied Biosystems). The primers preferably have appropriate restriction sites added thereto, in order to facilitate following cloning procedures.

One of the PCR reaction conditions may be the reaction of, for example, 30 cycles of 94° C. for 30 seconds (denaturation), 60° C. for 30 seconds to 1 minute (annealing) and 72° C. for 1 to 3 minutes (extension) followed by the reaction at 72° C. for 7 minutes. The amplified DNA fragments may then be cloned into an appropriate vector capable of amplifying in *E. coli*. Cloning may be carried out according to the standard method such as those described in Molecular Cloning, Second Edition; Current Protocols in Molecular Biology, Supplement 1-38, John Wiley & Sons (1987-1997) (hereinafter abbreviated as "Current Protocols in Molecular Biology"); and DNA Cloning 1: Core Techniques, A Practical Approach, Second Edition, Oxford University Press (1995) or with commercially available kits such as SuperScript Plasmid System for cDNA Synthesis and Plasmid Cloning (produced by Life Technologies Corp.) and ZAP-cDNA Synthesis Kit (produced by Stratagene Corp.).

Any cloning vector may be used as long as that can replicate in *E. coli* K12, such as phage vectors and plasmid vectors. The expression vector in *E. coli* may be used as a cloning vector. Specifically, the vectors described above may be used.

A plasmid containing a desired DNA may be obtained from the resulting transformant according to the standard method such as those described in Molecular Cloning, Second Edition; Current Protocols in Molecular Biology; and DNA Cloning 1: Core Techniques, A Practical Approach, Second Edition, Oxford University Press (1995). According to the above method, a nucleic acid molecule (for example, DNA) having a base sequence of SEQ ID NO: 1, SEQ ID NO: 2, SEQ ID NO: 4, SEQ ID NO: 6 or SEQ ID NO: 8 can be obtained.

A nucleic acid molecule having a base sequence of SEQ ID NO: 1, SEQ ID NO: 2, SEQ ID NO: 4, SEQ ID NO: 6 or SEQ ID NO: 8 in which one to several bases are deleted, substituted, added and/or inserted, wherein the base sequence encodes an enzyme protein having a particular activity may be isolated by utilizing, for example, a base sequence of a DNA fragment derived from an actinomycete that has the base sequence of SEQ ID NO: 1, SEQ ID NO: 2, SEQ ID NO: 4, SEQ ID NO: 6 or SEQ ID NO: 8 to screen a homologue of the DNA from other microorganisms under appropriate conditions. Alternatively, the above described mutated DNA may be prepared according to any methods known in the art such as chemical synthesis, gene engineering techniques and mutagenesis. Specifically, a mutated DNA may be obtained by artificially introducing a mutation into DNA having the base sequence of SEQ ID NO: 1, SEQ ID NO: 2, SEQ ID NO: 4, SEQ ID NO: 6 or SEQ ID NO: 8.

For example, DNA having the base sequence of SEQ ID NO: 1, SEQ ID NO: 2, SEQ ID NO: 4, SEQ ID NO: 6 or SEQ ID NO: 8 may be contacted with an agent that acts as a mutagen, may be irradiated with ultraviolet rays, or may be subjected to gene engineering techniques. Site specific mutagenesis, one of the gene engineering techniques, allows an introduction of a specific mutation at a specific position, and thus is useful, which can be carried out according to the methods described in, for example, Molecular Cloning Second Edition; Current Protocols in Molecular Biology; Nucleic Acids Research, 10, 6487 (1982); Nucleic Acids Research, 12, 9441 (1984); Nucleic Acids Research, 13, 4431 (1985); Nucleic Acids Research, 13, 8749 (1985); Proc. Natl. Acad. Sci. USA, 79, 6409 (1982); Proc. Natl. Acad. Sci. USA, 82, 488 (1985); and Gene, 102, 67 (1991).

(2) Obtaining Vectors, Transformants, and Enzymes

The vector of the present invention may be obtained by incorporating the above described DNA into a vector by standard genetic recombination techniques. The transformant of the present invention may be obtained by introducing the vector into a host cell by a method well known in the art. Further, the protein (enzyme) of the present invention can be obtained by culturing a transformant having a recombinant DNA in which the above DNA is integrated in a medium, and by allowing to produce the enzyme protein of the present invention involved in trehangelin synthesis in the culture medium.

In order to express a DNA fragment containing genes of the enzymes involved in trehangelin synthesis (3-ketoacyl-CoA synthase, 3-ketoacyl-CoA synthase, enoyl-CoA hydratase and acyltransferase) in a host cell, a DNA fragment containing the genes may be subjected to a restriction enzyme digestion or a DNase treatment to obtain a DNA fragment of appropriate length containing the genes, which may be inserted downstream of a promoter in an expression vector, and the obtained expression vector may be introduced into a host cell suitable for the expression vector.

The host cell used herein is not limited as far as the host cell can efficiently express the enzyme protein, and may be the host cell of the present invention as described above. The expression vector may be the vector of the present invention as described above.

A method for introducing a recombinant vector may be any method for introducing DNA into a host cell, for example an actinomycete, and examples of the method include a method using calcium ions [Proc. Natl. Acad. Sci. USA, 69, 2110 (1972)], the protoplast method (Japanese Patent Laid-Open No. S63-2483942) and methods described in Gene, 17, 107 (1982) and Molecular & General Genetics, 168, 111 (1979).

A transformant that has a recombinant DNA in which the above DNA is integrated may be cultured in a medium, and 3-ketoacyl-CoA synthase, 3-ketoacyl-CoA synthase, enoyl-CoA hydratase and acyltransferase of the present invention may be produced in the culture medium.

The transformant of the present invention transformed with the enzymes involved in trehangelin synthesis may be cultured according to common culturing methods used for the host cell employed. When the transformant of the present invention is prokaryotes such as *E. coli* and actinomycetes or eukaryotes such as yeasts, the medium for culturing the microorganisms may be any of natural media or synthetic media as far as the media contains carbon sources, nitrogen sources, inorganic salts and the like that could be used by the microorganisms, and as far as the media allow efficient culture of the transformant. For example, the medium for culturing actinomycetes may be any of natural media or synthetic media as far as the media contain carbon sources, nitrogen sources, inorganic salts and the like that could be used by the microorganisms, and as far as the media allow efficient culture of the transformant.

The carbon source may be the one that could be used by a host microorganism, and includes carbohydrates such as glucose, fructose, sucrose, molasses containing the foregoing, starch and starch hydrolysates; organic acids such as acetic acid and propionic acid; and alcohols such as ethanol and propanol.

The nitrogen source which may be used includes ammonia; ammonium salts of inorganic acids and organic acids such as ammonium chloride, ammonium sulphate, ammonium acetate and ammonium phosphate; other nitrogen-containing compounds, as well as peptone, meat extracts, yeast extract, corn steep liquor, casein hydrolysates, soybean meal and soybean meal hydrolysates, and various fermented cells and digested materials thereof.

The inorganic substance which may be used includes monopotassium phosphate, dipotassium phosphate, magnesium phosphate, magnesium sulphate, sodium chloride, ferrous sulphate, manganese sulphate, copper sulphate, calcium carbonate and the like.

Culture is carried out under an aerobic condition such as in shake culture or stirred submerged aerobic culture. The culture temperature is preferably 15 to 40° C. and the incubation period is usually 16 hours to 7 days. pH during culture is maintained at 3.0 to 9.0. pH is adjusted with an inorganic or organic acid, an alkaline solution, urea, calcium carbonate, ammonia and the like. During culture, an antibiotic such as ampicillin, tetracycline and thiostrepton may be optionally added to the medium.

In culturing an actinomycete transformed with an expression vector containing an inducible promoter, an inducer may be optionally added to the medium. For example, in case of an actinomycete transformed with an expression vector containing the lac promoter, isopropyl-β-D-thiogalactopyranoside (IPTG) and the like may be added to the medium, and when an actinomycete transformed with an expression vector containing the trp promoter is cultured, indoleacrylic acid (IAA) and the like may be added to the medium.

When the enzyme is produced inside of the host cells, the host cells are further homogenized. The obtained enzyme protein is, after disruption of the host cells purified to a desired purity using any combination of well-known protein purification techniques such as salting-out, dialysis, affinity chromatography, ion-exchange chromatography, size exclusion chromatography, organic solvent treatment, and heating treatment. The cells per se, a solution containing homogenate of the cells, or a soluble fraction of the homogenate may also be used as an enzyme provided these have no effect on reactions or reaction products.

In view of purification and manifestation of activity of an enzyme protein, the desired enzyme protein is preferably water-soluble. However, a water-insoluble enzyme protein may be solubilised according to the method known in the art such as addition of a surfactant. The desired protein may be expressed as a fusion protein with another protein (such as GST and TAG); however, a desired protein is preferably not a fusion protein.

(3) Production Method of Trehangelin

Trehangelin may be produced by producing and accumulating trehangelin in a culture medium of a transformant that is introduced the enzymes of the present invention involved in trehangelin synthesis. For example, in using an actinomycete as the host cell, trehalose may optionally be added during culture to a culture medium, although actinomycetes have the trehalose synthetic pathway. The host cells may be cultured according to the method described above for obtaining the enzymes.

Alternatively, trehangelin may be produced by using purified enzymes of the present invention involved in trehangelin synthesis. Thus, the present invention also encompasses a method for synthesizing trehangelin at least comprising reacting angelyl-CoA with trehalose in the presence of an enzyme protein (orfC) having an amino acid sequence of SEQ ID NO: 7 (or an amino acid sequence having 60% or more identity with the amino acid sequence of SEQ ID NO: 7 or an amino acid sequence of SEQ ID NO: 7 in which one to several amino acids are deleted, substituted, added and/or inserted. The method for synthesizing trehangelin of the present invention may further comprise one to three steps selected from the following (i) to (iii): (i) reacting acetyl-CoA with methylmalonyl-CoA in the presence of an enzyme protein (orfB) having an amino acid sequence of SEQ ID NO: 5 (or an amino acid sequence having 60% or more identity with the amino acid sequence of SEQ ID NO: 5 or an amino acid sequence of SEQ ID NO: 5 in which one to several amino acids are deleted, substituted, added and/or inserted) to obtain 2-methylacetoacetyl-CoA; (ii) reacting 2-methylacetoacetyl-CoA with NADPH in the presence of an enzyme protein (orfD) having an amino acid sequence of SEQ ID NO: 9 (or an amino acid sequence having 60% or more identity with the amino acid sequence of SEQ ID NO: 9 or an amino acid sequence of SEQ ID NO: 9 in which one to several amino acids are deleted, substituted, added and/or inserted) to obtain 3-hydroxy-2-methylbutyryl-CoA; and (iii) converting 3-hydroxy-2-methylbutyryl-CoA to angelyl-CoA into the presence of an enzyme protein (orfA) having an amino acid sequence of SEQ ID NO: 3 (or an amino acid sequence having 60% or more identity with the amino acid sequence of SEQ ID NO: 3 or an amino acid sequence of SEQ ID NO: 3 in which one to several amino acids are deleted, substituted, added and/or inserted). The reaction using the enzymes may be carried out according to the method described hereinbelow for the enzyme activity assay of the protein.

Trehangelin may be isolated and purified from the culture medium of the transformant of the present invention according to the method described in Japanese Patent Laid-Open No. 2015-024985, namely an appropriate combination of separation of cells, extraction, distillation, chromatography and the like.

(4) Enzyme Activity Assay of the Protein

Enzyme activity of the obtained protein may be assayed according to a common enzyme activity assay. A buffer used for a reaction solution of the activity assay may have pH in the range that does not inhibit the activity of the target enzyme, and preferably has pH in the range including an optimal pH.

Any buffer that does not inhibit the enzyme activity and can attain the above pH may be used. The buffer which may be used includes Tris hydrochloride buffer, phosphate buffer, borate buffer, HEPES buffer, MOPS buffer, hydrogen carbonate buffer and the like. The concentration of the buffer may be any concentration as far as it does not inhibit the enzyme activity and is suitably 1 mM to 1 M.

A substrate of the target enzyme is added to the reaction solution. Specifically, in a 3-ketoacyl-CoA synthase activity assay, acetyl-CoA and methylmalonyl-CoA are added. In a 3-ketoacyl-CoA reductase activity assay, 2-methylacetoacetyl-CoA is added. In an enoyl-CoA hydratase activity assay, 3-hydroxy-2-methylbutyryl-CoA is added. In an acyltransferase activity assay, angelyl-CoA is added. The concentration of the substrate may be any concentration as far as it has no effect on the reaction, and is suitably 0.01 mM to 0.2 M of the reaction solution. The enzyme concentration for the reaction is not particularly limited, and is usually in a range of 0.001 mg/ml to 100 mg/ml. It is not always required that the enzyme used is purified to consisting of a single type of protein, and an authentic preparation containing other contaminated proteins may be used as far as they do not interfere with the reaction.

The reaction temperature may be in the range that does not inhibit the activity of the utilized enzyme, and is preferably in the range including an optimal temperature of the enzyme. Thus, the reaction temperature can be 10° C. to 60° C., and more preferably 27° C. to 40° C.

The activity may be detected by a method that can measure a decrease of substrates or an increase of reaction products during the reaction. Examples of such methods include a method that separates and quantifies a target substance optionally by using thin layer chromatography, column chromatography, high-performance liquid chromatography (HPLC) and the like. The reaction product may be identified by a method separating the target substance with thin layer chromatography, column chromatography, HPLC and the like, and then comparing the retention time of the target substance with that of an authentic preparation, or by a method employing a nuclear magnetic resonator or a mass spectrometer.

(5) Production Method of Angelyl-CoA

The present invention is further directed to a method for producing angelyl-CoA by using 3-ketoacyl-CoA synthase, 3-ketoacyl-CoA reductase and/or enoyl-CoA hydratase of the present invention. In this production method, 3-ketoacyl-CoA synthase, 3-ketoacyl-CoA reductase and/or enoyl-CoA hydratase, and three substrates, i.e. acetyl-CoA, methylmalonyl-CoA and reduced nicotinamide adenine dinucleotide phosphate (NADPH) are appropriately added into a solution to allow appropriate reactions, thereby angelyl-CoA may be produced. More specifically, the method for producing angelyl-CoA of the present invention may comprise one to all steps selected from (i) to (iii) described hereinabove for the method for synthesizing trehangelin. It is conceived that esters of angelic acid may be used for antipyretic analgesics, muscle relaxants, sedatives and the like.

The present invention is more specifically described hereinbelow by way of Examples which do not limit the scope of the present invention. All documents cited herein are entirely incorporated herein by reference.

EXAMPLES (Analytical Method)

In the following Examples, LC/MS analysis was carried out under the following conditions:

Column: Inertsil ODS-4 (produced by GL Sciences Inc.), size: diameter 3.0 mm×length 250 mm, 40° C.

Mobile phase: 2 mM ammonium acetate aqueous solution (A), 2 mM ammonium acetate-containing methanol solution (B), 0-5 minutes 5% B, 5-35 minutes 5-100% B, 35-40 minutes 100% B, flow rate: 0.5 ml/min.

Detection: QSTAR Elite ESI quadruple time-of-flight (Q-TOF) MS instrument (produced by AB Sciex).

[Example 1] Production of Trehangelin from Actinomycete Cloned with DNA of SEQ ID NO: 1

The K07-0510 strain was cultured in YD medium containing 1% yeast extract and 1% glucose at an appropriate temperature (for example, 27° C.) for a few days. After culturing, cells were collected from the resulting culture medium by centrifugation and the chromosomal DNA was isolated and purified from the cells according to the standard method (Molecular Cloning, Second Edition).

Four open reading frames (orfs) on SEQ ID NO: 1 were named as orfA, orfB, orfC and orfD in the order of the base positions. The positions and functions of orfA to D in SEQ ID NO: 1 are as follows:

orfA (SEQ ID NO: 2: positions 1-828 in SEQ ID NO: 1, encoding enoyl-CoA hydratase)
orfB (SEQ ID NO: 4: positions 875-1900 in SEQ ID NO: 1, encoding 3-ketoacyl-CoA synthase)
orfC (SEQ ID NO: 6: positions 1905-2684 in SEQ ID NO: 1, encoding acyltransferase)
orfD (SEQ ID NO: 8: positions 2681-3475 in SEQ ID NO: 1, encoding 3-ketoacyl-CoA reductase)

A recombinant plasmid sufficiently expressing the above four genes was constructed by PCR [Science, 230, 1350 (1985)] as described hereinbelow.

A DNA capable of expressing orfA, orfB, orfC and orfD (hereinafter referred to as "orfABCD") was amplified by carrying out PCR on a DNA Thermal Cycler (produced by Applied Biosystems) with using the chromosomal DNA of an actinomycete *Polymorphospora rubra* K07-0510 as a template, a sense primer of SEQ ID NO: 10 having a PstI restriction enzyme site and a ribosome binding sequence at its 5'-terminal, an antisense primer of SEQ ID NO: 11 having a StuI restriction enzyme site at its 5'-terminal, and Taq DNA polymerase (produced by Roche Life Science). The condition of PCR was 30 cycles of 95° C. for 30 seconds, 68° C. for 30 seconds, and 72° C. for 4 minute followed by 72° C. for 10 minutes. The amplified DNA fragment was purified by agarose gel electrophoresis, and digested with restriction enzymes PstI and StuI to obtain a DNA fragment (hereinafter referred to as "orfABCD-containing DNA fragment") containing a PstI and StuI-treated DNA expressing orfABCD.

pOSV556t [Nat. Chem., 3, 338 (2011)] was digested with restriction enzymes PstI and StuI to obtain a PstI and StuI-treated pOSV556t fragment. The PstI and StuI-treated orfABCD-containing DNA fragment obtained above and the PstI and StuI-treated pOSV556t fragment were mixed and ligated to obtain a recombinant DNA.

The recombinant DNA was used to transform *E. coli* Top10 according to the standard method, and the transformant was applied on a LB agar medium containing 100 µg/ml ampicillin, and incubated overnight at 37° C. A plasmid containing the recombinant DNA was isolated from the transformant according to the standard method. The recombinant DNA was sequenced to confirm that the DNA was orfABCD, and the plasmid was named as pOSV556-orfABCD.

The pOSV556-orfABCD was introduced into *E. coli* ET12567/pUZ8002 [Practical *Streptomyces* Genetics (2000)] according to the standard method to obtain *E. coli* ET12567/pUZ8002/pOSV556-orfABCD that is resistant to 50 µg/ml kanamycin, 25 µg/ml chloramphenicol and 100 µg/ml ampicillin. The pOSV556-orfABCD was further transferred by conjugation according to the standard method from *E. coli* ET12567/pUZ8002 to an actinomycete *Streptomyces albus* J1074 to obtain *Streptomyces albus*/pOSV556-orfABCD resistant to 50 µg/ml hygromycin.

*Streptomyces albus*/pOSV556-orfABCD was grown by shake culture in 10 ml of a liquid medium containing 1% yeast extract and 1% glucose at 27° C. for 1 day, which was then added 1 ml of 20% trehalose aqueous solution, and the shake culture was continued at 27° C. for 4 more days. The obtained culture medium was added 10 ml of ethanol and stirred for 1 hour. Ethanol in the extract was then removed by distillation under reduced pressure, and 5 ml of ethyl acetate was added to the obtained aqueous solution, which was thoroughly stirred, and then the ethyl acetate phase was collected. After concentration to dryness, the solid was dissolved in 100 µl of methanol and analysed on LC/MS to confirm production of trehangelin (FIG. 1).

[Example 2] Confirmation of Function of the Enzyme Protein (orfB) Encoded by the Base Sequence of SEQ ID NO: 4

A recombinant plasmid sufficiently expressing a gene encoding 3-ketoacyl-CoA synthase (orfB) was constructed by PCR [Science, 230, 1350 (1985)] as described hereinbelow.

orfB was amplified by carrying out PCR on a DNA Thermal Cycler (produced by Applied Biosystems) with using the chromosomal DNA of an actinomycete *Polymorphospora rubra* K07-0510 as a template, a sense primer of SEQ ID NO: 12 and having a NdeI restriction enzyme site at its 5'-terminal, an antisense primer of SEQ ID NO: 13 and having a XhoI restriction enzyme site at its 5'-terminal and Taq DNA polymerase (produced by Roche Life Science). PCR was carried out under the conditions of 30 cycles of 95° C. for 30 seconds, 60° C. for 30 seconds and 72° C. for 1 minute followed by 72° C. for 10 minutes. The amplified DNA fragment was purified by agarose gel electrophoresis, and digested with restriction enzymes NdeI and XhoI to obtain a NdeI and XhoI-treated orfB-containing DNA fragment.

pET-15b (produced by Novagen) was digested with restriction enzymes NdeI and XhoI to obtain a NdeI and XhoI-treated pET-15b fragment. The NdeI and XhoI-treated orfB-containing DNA fragment obtained above and the NdeI and XhoI-treated pET-15b fragment were mixed and ligated to obtain a recombinant DNA.

The recombinant DNA was used to transform *E. coli* Top10 according to the standard method, and the transformant was applied on a LB agar medium containing 100 µg/ml ampicillin, which was incubated overnight at 37° C. A plasmid containing the recombinant DNA was isolated from the transformant according to the standard method. Sequencing of the obtained DNA showed that the DNA had the base sequence of SEQ ID NO: 4, thereby the recombinant DNA was confirmed to have orfB, and the plasmid was named as pET-15b-orfB.

The pET-15b-orfB was introduced into *E. coli* BL21 (DE3) having DE3 (produced by Novagen) according to the standard method to obtain BL21(DE3)/pET-15b-orfB resistant to 100 µg/ml ampicillin. BL21(DE3)/pET-15b-orfB was cultured in 200 ml of a LB liquid medium containing 100 µg/ml ampicillin at 37° C. until the turbidity at 600 nm reached 0.5, and then the culture medium was stored in a refrigerator for 2 hours, followed by addition of isopropyl thiogalactoside at a final concentration of 0.5 mM. After an additional culture at 18° C. for 16 hours, the culture supernatant was removed by centrifugation (9000 rpm, 2 min). The cells were suspended in 10 ml of washing buffer [20 mM Tris hydrochloride (pH 8.0), 100 mM NaCl, 50 mM imidazole and 10% glycerol], to which 10 µl of 90 mg/ml phenylmethylsulfonyl fluoride (PMSF) was added, and the cells were disrupted on an ultrasonicator (produced by Wakenyaku Co., Ltd.) on ice. The obtained cell homogenate was centrifuged (10,000 rpm, 20 min, 4° C.) to obtain a supernatant. The supernatant obtained after centrifugation of the cell extract was applied on Ni Sepharose 6 Fast Flow resin (produced by GE Healthcare), and the resin was washed with 20 ml of the washing buffer. An elution buffer [20 mM Tris hydrochloride (pH 8.0), 100 mM NaCl, 500 mM imidazole and 10% glycerol] 5 ml was applied to the column to allow elution. The eluent was concentrated by using an Amicon Ultra Centrifugal Filter (produced by Merck).

Next, it was examined whether the obtained recombinant enzyme protein (OrfB) catalyses production of 2-methylacetoacetyl-CoA from acetyl-CoA and methylmalonyl-CoA by employing the following reaction conditions. A reaction solution (100 µl) containing 100 mM phosphate buffer (pH 7.5), 250 µM acetyl-CoA, 250 µM methylmalonyl-CoA and 2.5 µg orfB was prepared, and subjected to a reaction at 27° C. for 16 hours. After termination of the reaction by adding 100 µl of methanol, it was analysed on LC/MS.

Figure 2:
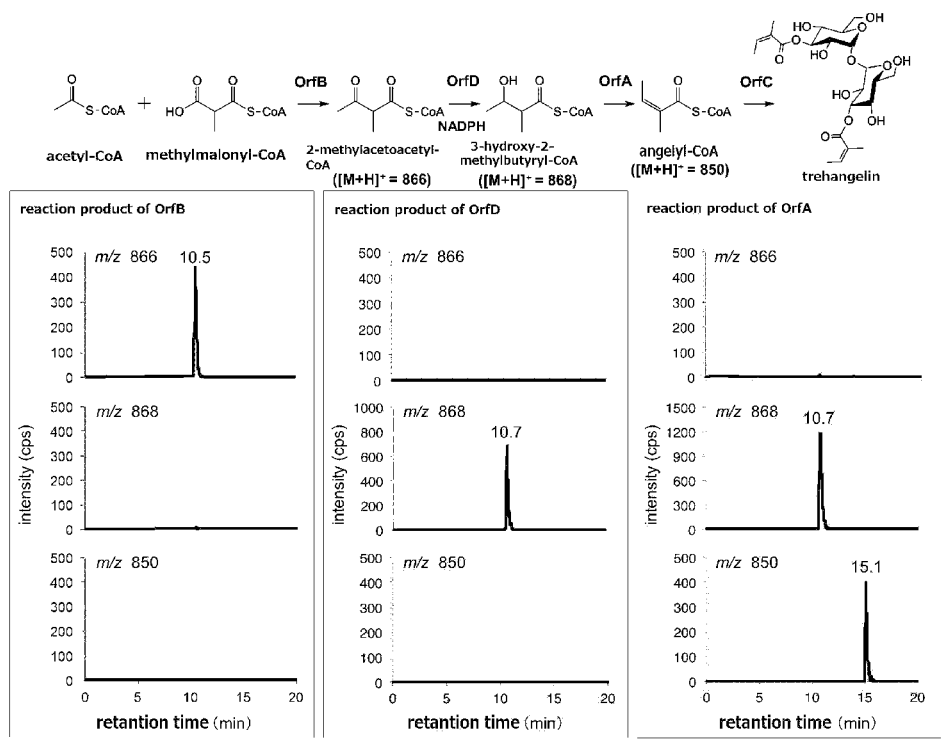
FIG. 2 shows the result of detection of a reaction product of orfB, orfD and orfA by LC/MS.

As a result, production of 2-methylacetoacetyl-CoA was observed (FIG. 2). The result indicates that OrfB catalyses production of 2-methylacetoacetyl-CoA from acetyl-CoA and methylmalonyl-CoA, and thus it was confirmed that the obtained enzyme protein was 3-ketoacyl-CoA synthase.

[Example 3] Confirmation of Function of the Enzyme Protein (orfD) Encoded by the Base Sequence of SEQ ID NO: 8

A recombinant plasmid sufficiently expressing a gene encoding 3-ketoacyl-CoA reductase (orfD) was constructed by PCR [Science, 230, 1350 (1985)] as described hereinbelow. OrfD was amplified by carrying out PCR on a DNA Thermal Cycler (produced by Applied Biosystems) with using the chromosomal DNA of an actinomycete *Polymorphospora rubra* K07-0510 as a template, a sense primer of SEQ ID NO: 14 having a NdeI restriction enzyme site at its 5'-terminal, an antisense primer of SEQ ID NO: 15 having a XhoI restriction enzyme site at its 5'-terminal, and Taq DNA polymerase (produced by Roche Life Science). The condition of PCR was 30 cycles of 95° C. for 30 seconds, 60° C. for 30 seconds, and 72° C. for 1 minute followed by 72° C. for 10 minutes. The amplified DNA fragment was purified by agarose gel electrophoresis, and digested with restriction enzymes NdeI and XhoI to obtain a NdeI and XhoI-treated orfD-containing DNA fragment.

pET-15b (produced by Novagen) was digested with restriction enzymes NdeI and XhoI to obtain a NdeI and XhoI-treated pET-15b fragment. The NdeI and XhoI-treated orfD-containing DNA fragment obtained above and the NdeI and XhoI-treated pET-15b fragment were mixed and ligated to obtain a recombinant DNA.

The recombinant DNA was used to transform *E. coli* Top10 according to the standard method, and the transformant was applied on a LB agar medium containing 100 μg/ml ampicillin, which was incubated overnight at 37° C. A plasmid containing the recombinant DNA was isolated from the transformant according to the standard method. DNA Sequencing showed the DNA had base sequence of SEQ ID NO: 8, thereby the recombinant DNA was confirmed to have orfD, and the plasmid was termed pET-15b-orfD.

The pET-15b-orfD was introduced into *E. coli* BL21 (DE3) having DE3 (produced by Novagen) according to the standard method to obtain BL21(DE3)/pET-15b-orfD resistant to 100 μg/ml ampicillin. BL21(DE3)/pET-15b-orfD was cultured in 200 ml of a LB liquid medium containing 100 μg/ml ampicillin at 37° C. until the turbidity at 600 nm reached 0.5, and then the culture medium was stored in a refrigerator for 2 hours, followed by addition of isopropyl thiogalactoside at a final concentration of 0.5 mM. After an additional culture at 18° C. for 16 hours, the culture supernatant was removed by centrifugation (9000 rpm, 2 minutes). The cells were suspended in 10 ml of washing buffer [20 mM Tris hydrochloride (pH 8.0), 100 mM NaCl, 50 mM imidazole and 10% glycerol], to which 10 μl of 90 mg/ml PMSF was added, and the cells were disrupted on an ultrasonicator (produced by Wakenyaku Co., Ltd.) on ice. The obtained cell homogenate was centrifuged (10,000 rpm, 20 minutes, 4° C.) to obtain a supernatant. The supernatant obtained after centrifugation of the cell extract was applied on Ni Sepharose 6 Fast Flow resin (produced by GE Healthcare), and the resin was washed with 20 ml of the washing buffer. An elution buffer [20 mM Tris hydrochloride (pH 8.0), 100 mM NaCl, 500 mM imidazole and 10% glycerol] 5 ml was applied to the column to allow elution. The eluent was concentrated by using an Amicon Ultra Centrifugal Filter (produced by Merck).

Next, it was examined whether the obtained recombinant enzyme protein (OrfD) catalysed production of 3-hydroxy-2-methylbutyryl-CoA from 2-methylacetoacetyl-CoA by employing the following reaction conditions. A reaction solution (100 μl) containing 100 mM phosphate buffer (pH 7.5), 250 μM acetyl-CoA, 250 μM methylmalonyl-CoA, 500 μM NADPH, 2.5 μg orfB (obtained in Example 2) and 0.8 μg orfD was prepared, and subjected to a reaction at 27° C. for 16 hours. After termination of the reaction by adding 100 μl of methanol, it was analysed on LC/MS.

As a result, production of 3-hydroxy-2-methylbutyryl-CoA was observed (FIG. 2). The result indicates that OrfD catalyses production of 3-hydroxy-2-methylbutyryl-CoA from 2-methylacetoacetyl-CoA, and thus it was confirmed that the obtained enzyme protein was 3-ketoacyl-CoA reductase.

[Example 4] Confirmation of Function of the Enzyme Protein (orfA) Encoded by the Base Sequence of SEQ ID NO: 2

A recombinant plasmid sufficiently expressing a gene encoding enoyl-CoA hydratase (orfA) was constructed by PCR [Science, 230, 1350 (1985)] as described hereinbelow. OrfA was amplified by carrying out PCR on a DNA Thermal Cycler (produced by Applied Biosystems) with using the chromosomal DNA of an actinomycete *Polymorphospora rubra* K07-0510 as a template, a sense primer of SEQ ID NO: 16 having a NdeI restriction enzyme site at its 5'-terminal, an antisense primer of SEQ ID NO: 17 having a BamHI restriction enzyme site at its 5'-terminal, and Taq DNA polymerase (produced by Roche Life Science). The condition of PCR was 30 cycles of 95° C. for 30 seconds, 60° C. for 30 seconds and 72° C. for 1 minute followed by 72° C. for 10 minutes. The amplified DNA fragment was purified by agarose gel electrophoresis, and digested with restriction enzymes NdeI and BamHI to obtain a NdeI and BamHI-treated orfA-containing DNA fragment.

pET-15b (produced by Novagen) was digested with restriction enzymes NdeI and BamHI to obtain a NdeI and BamHI-treated pET-15b fragment. The NdeI and BamHI-treated orfA-containing DNA fragment obtained above and the NdeI and BamHI-treated pET-15b fragment were mixed and ligated to obtain a recombinant DNA.

The recombinant DNA was used to transform *E. coli* Top10 according to the standard method, and the transformant was applied on a LB agar medium containing 100 μg/ml ampicillin, and incubated overnight at 37° C. A plasmid containing the recombinant DNA was isolated from the transformant according to the standard method. Sequencing showed the DNA had the base sequence of SEQ ID NO: 2, thereby the recombinant DNA was confirmed to have orfA, and the plasmid was termed pET-15b-orfA.

The pET-15b-orfA was introduced into *E. coli* BL21 (DE3) having DE3 (produced by Novagen) according to the standard method to obtain BL21(DE3)/pET-15b-orfA resistant to 100 μg/ml ampicillin. BL21(DE3)/pET-15b-orfA was cultured in 200 ml of a LB liquid medium containing 100 μg/ml ampicillin at 37° C. until the turbidity at 600 nm reached 0.5, and then the culture medium was stored in a refrigerator for 2 hours, followed by addition of isopropyl thiogalactoside at a final concentration of 0.5 mM. After an additional culture at 18° C. for 16 hours, the culture supernatant was removed by centrifugation (9000 rpm, 2 minutes). The cells were suspended in 10 ml of washing buffer [20 mM Tris hydrochloride (pH 8.0), 100 mM NaCl, 50 mM imidazole and 10% glycerol], to which 10 μl of 90 mg/ml PMSF was added, and the cells were disrupted on an ultrasonicator (produced by Wakenyaku Co., Ltd.) on ice. The obtained cell homogenate was centrifuged (10,000 rpm, 20 minutes, 4° C.) to obtain a supernatant. The supernatant obtained after centrifugation of the cell extract was applied on Ni Sepharose 6 Fast Flow resin (produced by GE Healthcare), and the resin was washed with 20 ml of the washing buffer. An elution buffer [20 mM Tris hydrochloride (pH 8.0), 100 mM NaCl, 500 mM imidazole and 10% glycerol] 5 ml was applied to the column to allow elution. The eluent was concentrated by using an Amicon Ultra Centrifugal Filter (produced by Merck).

Next, it was examined whether the obtained recombinant enzyme protein (OrfA) catalysed production of angelyl-CoA from 3-hydroxy-2-methylbutyryl-CoA by employing the following reaction conditions. A reaction solution (100 μl) containing 100 mM phosphate buffer (pH 7.5), 250 μM acetyl-CoA, 250 μM methylmalonyl-CoA, 500 μM NADPH, 2.5 μg orfB (obtained in Example 2), 0.8 μg orfD (obtained in Example 3) and 15.8 μg orfA was prepared and subjected to a reaction at 27° C. for 16 hours. After termination of the reaction by adding 100 μl of methanol, it was analysed on LC/MS.

As a result, production of angelyl-CoA was observed (FIG. 2). The result indicates that OrfA catalyses production of angelyl-CoA from 3-hydroxy-2-methylbutyryl-CoA, and thus it was confirmed that the obtained enzyme protein was enoyl-CoA hydratase.

As described above, it was showed that expression of OrfA, OrfB, OrfC and OrfD in combination produced trehangelin in Example 1. It was also showed that OrfB produced 2-methylacetoacetyl-CoA by reacting acetyl-CoA with methylmalonyl-CoA, that OrfD converted 2-methylacetoacetyl-CoA to 3-hydroxy-2-methylbutyryl-CoA, and that OrfA converted 3-hydroxy-2-methylbutyryl-CoA to angelyl-CoA, in Examples 2 to 4. These show that OrfC produced trehangelin by reacting angelyl-CoA with trehalose in the test system of Example 1, in other words, OrfC had an acyltransferase activity.

[Example 5] Production of Trehangelin in Corynebacteria

Trehangelin was produced in *Corynebacterium glutamicum*.
(1) Analytical Method
Column: YMC-PACK ODS-AQ 250×4.6 mm S-5 mm, 12 nm, 30° C. Mobile phase: 0.1% formic acid (A), acetonitrile (B), 15% B, 30 minutes, 0.5 mL/min
Detection: Agilent 6224 TOF LC/MS (Agilent Technologies)
(2) Introduction of Trehangelin Biosynthesis Enzyme Genes into *Corynebacterium glutamicum*

The nucleic acid sequences of SEQ ID NO: 18 and SEQ ID NO: 19 were designed as the sequences of orfAB and orfCD in which codon usage was optimized to *Corynebacterium glutamicum*. Based on the designed nucleic acid sequences, nucleic acid molecules encoding orfAB and orfCD were artificially synthesized. Then orfABCD were linked and inserted into a vector.

Specifically, orfAB and orfCD were respectively amplified by PCR with using PrimeSTAR Max DNA Polymerase (TAKARA) and using respective primers for orfAB and orfCD, reacting at 98° C. for 1 minute followed by 30 cycles of one cycle reaction at 98° C. for 10 seconds and at 68° C. for 30 seconds. The orfAB primers and orfCD primers used are as follows:

```
orfAB primer (forward):
                              (SEQ ID NO: 20)
AGAGGAGACACAACGAGCTCATGTCCGTTTCCCGCGTTG orfAB primer (reverse):
                              (SEQ ID NO: 21)
AGCGGAGGTGGTCATCACTTTAGCGAACGCAGTTG orfCD primer (forward):
                              (SEQ ID NO: 22)
ATGACCACCTCCGCTCTG orfCD primer (reverse):
                              (SEQ ID NO: 23)
CCGATATCCTGCAGGAGCTCTTAGCCCAGGCCGTAGCC.
```

The obtained PCR fragments were purified with Gel/PCR extraction kit (Japan). The purified PCR fragments were mixed with a vector digested with SacI, and two gene fragments were ligated using In-Fuion HD Cloning Kit as simultaneously inserting into the vector. The vector used was pYTKA9-PgapA containing the gapA gene promoter. pYTKA9-PgapA was obtained by artificially creating the pBL1 ori, a typical ori for corynebacteria (Santamaria, R., Gil, J. A., Mesase, J. M. and Martin, J. F. (1984) J. Gen. Microbiol. 130, 2237-2246.), which was introduced into pHSG298 vector (Takara Bio Inc.) with the gapA gene promoter (Hasegawa et al., Appl Environ Microbiol. (2012) 78(3): 865-75). The obtained vector containing nucleic acid molecules encoding orfAB and orfCD was used to transform *E. coli* HST02 in the LB medium containing kanamycin (50 μg/mL). Further, *Corynebacterium glutamicum* ATCC 13032 was transformed by electroporation to obtain *Corynebacterium glutamicum* having trehangelin biosynthesis enzyme genes.

(3) Preculture of *Corynebacterium glutamicum*

A glycerol stock of *Corynebacterium glutamicum* ATCC 13032 having trehangelin biosynthesis enzyme genes prepared above was added to 5 mL of BHI medium containing 37 g of brain heart infusion in 1000 mL of pure water. *Corynebacterium glutamicum* was cultured while shaking at 30° C. and 180 rpm for 24 hours to obtain a preculture solution.

(4) Main Culture of *Corynebacterium glutamicum*

The preculture solution at the amount of 3% was added to a Sakaguchi Flask containing 50 mL of BHI medium, which was added 2.5 mL of 400 g/L glucose solution so that the initial concentration of glucose at the start of the culture became 20 g/L. At 24 and 48 hours after starting the culture, 2.5 mL of the same glucose solution was added. 100 g/L trehalose solution was added 1 mL at the start of the culture, and added 0.25 mL at each of 24 and 48 hours after the start of the culture. In order to adjust pH, 1.25 mL of 20% calcium carbonate solution was added at 4 and 24 hours after the start of the culture. Culture was carried out at 30° C. for 72 hours with shaking at 180 rpm.

(5) Analysis of Culture Supernatant

The culture supernatant at 72 hours after the start of the main culture was analysed by LC/MS, and a peak of trehangelin was detected at the same retention time as the authentic preparation.

What is claimed is:

1. A vector comprising a nucleic acid molecule having at least one base sequence selected from the following (i) to (iv) (i) a base sequence of SEQ ID NO: 2, a base sequence encoding an amino acid sequence of SEQ ID NO: 3, or a base sequence having 90% or more identity with the base sequence of SEQ ID NO: 2 wherein a protein encoded by the base sequence has a 3-ketoacyl-CoA synthase activity; (ii) a base sequence of SEQ ID NO: 4, a base sequence encoding an amino acid sequence of SEQ ID NO: 5, or a base sequence having 90% or more identity with the base sequence of SEQ ID NO: 4 wherein a protein encoded by the base sequence has a 3-ketoacyl-CoA reductase activity; (iii) a base sequence of SEQ ID NO: 6, a base sequence encoding an amino acid sequence of SEQ ID NO: 7, or a base sequence having 90% or more identity with the base sequence of SEQ ID NO: 6 wherein a protein encoded by the base sequence has an enoyl-CoA hydratase activity; and (iv) a base sequence of SEQ ID NO: 8, a base sequence encoding an amino acid sequence of SEQ ID NO: 9, or a base sequence having 90% or more identity with the base sequence of SEQ ID NO: 8 wherein a protein encoded by the base sequence has an acyltransferase activity.

2. A transformant comprising the vector of claim 1.

3. The transformant of claim 2, which is *Escherichia*.

4. A method for producing trehangelin comprising culturing the transformant of claim 2 to produce trehangelin.

5. The vector of claim 1, wherein the nucleic acid molecule comprises all of the base sequences of (i) to (iv) as recited in claim 1.

6. The vector of claim 1, wherein the nucleic acid molecule has a base sequence of SEQ ID NO: 1, or a base sequence having 90% or more identity with the base sequence of SEQ ID NO: 1 wherein a protein encoded by the base sequence has a 3-ketoacyl-CoA synthase activity, 3-ketoacyl-CoA reductase activity, enoyl-CoA hydratase activity, and acyltransferase activity.

7. The vector of claim 1, wherein the nucleic acid molecule has a base sequence of SEQ ID NO: 2, a base sequence encoding an amino acid sequence of SEQ ID NO: 3, or a base sequence having 90% or more identity with the base sequence of SEQ ID NO: 2 wherein a protein encoded by the base sequence has a 3-ketoacyl-CoA synthase activity.

8. The vector of claim 1, wherein the nucleic acid molecule has a base sequence of SEQ ID NO: 4, a base sequence encoding an amino acid sequence of SEQ ID NO: 5, or a base sequence having 90% or more identity with the base sequence of SEQ ID NO: 4 wherein a protein encoded by the base sequence has a 3-ketoacyl-CoA reductase activity.

9. The vector of claim 1, wherein the nucleic acid molecule has a base sequence of SEQ ID NO: 6, a base sequence encoding an amino acid sequence of SEQ ID NO: 7; or a base sequence having 90% or more identity with the base sequence of SEQ ID NO: 6 wherein a protein encoded by the base sequence has an enoyl-CoA hydratase activity.

10. The vector of claim 1, wherein the nucleic acid molecule has a base sequence of SEQ ID NO: 8, a base sequence encoding an amino acid sequence of SEQ ID NO: 9, or a base sequence having 90% or more identity with the base sequence of SEQ ID NO: 8 wherein a protein encoded by the base sequence has an acyltransferase activity.

* * * * *

SEQUENCE LISTING

<160> NUMBER OF SEQ ID NOS: 23

<210> SEQ ID NO 1
<211> LENGTH: 3475
<212> TYPE: DNA
<213> ORGANISM: Polymorphospora rubra K07-0510

<400> SEQUENCE: 1

```
gtgacccgac cggacgcccc gggcccaccg gtcgccgccc cggacccggc cgacgccgtc        60
gtgacggccg tcgagccgta cgtggtccgg gcgacgatca accgaccggc ccgccgcaac       120
gccatcgacc tcgccgtgat cgagggcctc gaacgcgcca tcgacctcgc cgaggcgacc       180
ggcgccgggt cctggtgct gcgcggcgcc ggcggcacct tctgctccgg cgccgacctg        240
cgcgtcctgg aggagatgag cgtcgacccg caccgggtgg agacgttcat ggtgcggctc       300
gccctcgtgc tgcgccggct ggagaccgcc cggttcgtct cggtcgcggt cgtcgagggg       360
cacgccgtcg cgggcggctg cgagatcctg ctcgcctgcg acgtctcggt cgccgccacc       420
gacgcccgca tcggcgaccg ccatctcgag tacgggctgg tccccgccgc cggcggctcg       480
gtacggctgg cccgcaccct gcccaaggcc cggggcaact acctgctgct cgccgccgac       540
ctgctcaccg gggagcaggc ggcgcagtgg ggactggtca gcgtcgcggt gccgccaacc       600
gacctggaac cccgggtgga cgccctggtc gggcggctcg tcggccacag cgccgacgcg       660
ctcgccgtgg tcaagaagat ggtctggacc gccgaccacg aaccccggcc ggacgccatg       720
tcctgggaac gccggctctt cctgcgccac ctcggctccg aagacgtgtc cgaggggctg       780
cgcgccttcc gcgagcggcg ccggccggcg ttccgcgccg atgactgact ccgtacggcc       840
gcccgaccgg acgcccgac cgcaaggaga ccacatgtcg acctcgacgg tgatcggaac       900
aggttcgtac ctaccccgcc gcgtcctcag cagcggcgaa ctggcccgcc gggtcggtgt       960
ggcggagaac tggatcgtgg agaagaccgg gatccgggaa cgccgggtgg ccgccgacga      1020
ggaggccacc tccgacctgg ccacccgggc cgcgcgccgg cgcgctgcgga ccgcccggct      1080
ggacccggcc gacgtcgacc tgatcgtgct ggcgacctcc acaccggacc ggccgatgcc      1140
ggccaccgcc agcaccgtgc aggccaacct cggcgcccgc caggcggtcg cgttcgacgt      1200
cgacgcggtg tgcagcggct tcgtgtacgc cctcgtcgtc gcccactcga tgctgaacag      1260
cgagggctgg gcccgtaccg cgctggtgat cggcgccgac acgtactcgc gggtcctgga      1320
ctacaccgac cggcgtaccg cggtgctctt cggcgacggt gccggcgcgg tcgtcctcgg      1380
ccgggagacc ggcggcggga gcggaatccg ggccaccacc ctgggcaccg acggcaccct      1440
cgccgacctc gtccagatcc cggcggcgg cagccgccgg ccggcgagcg cgcagacggt      1500
cgaggccggc gaccactact tcgcgatgcg cggcggcgac gtccgcaggc tggccaacca      1560
ggtcttcccg gcactggtcg ggcaactgct caaggcggcc tcgctcgacc tggaccaggt      1620
cgacctgatc gccgcccacc aggccaacgg cacgatgctc accgactggt cgcgggacct      1680
cggcctgcgc ccgggggtgc tgcaccgcac cgtcgagcgg tacggcaaca ccggtgccgc      1740
ctcggtcccg gtcaccctcg acgacgccgt acgcaccggg cggctcggtg ccgccgccac      1800
cctgctgatg gtcgccttcg gcggcgggat gacctggggc ggcgtcgccc tggactggtc      1860
cgccgacccg tcggttcccc gctccaactg cgtgaggtga agtgatgacc acgtccgcac      1920
tcggcgccga accgggcgcc accgatccgc cggccgcccc gccggtctcc tacgccccgt      1980
ccggccggat gccccggacg atcaaccgct ggccgcgccc gttcgcgccg cgcaacatcc      2040
tcggcgtgct gcgggcccgg ctgcgcggcg ccacgatcag cctcaaccag gtcaagttcg      2100
```

-continued

```
acgagtccac cgcggagcgc aacgcgctgg tgatggaaca cgcgctgctg cggcacagcc    2160
acgtcgcccg gtacgcgatc gtcggcccgt tcacctcgct gttcaaggtc cgggtcggcc    2220
cgtacgccgg gatcgccgag aaggtgaccg tcggtgccct gccgcactgg ccggaactgc    2280
cgaccagtca cgtcttcccg gtcaacgccg agttcggctt ctgcgcgggg gagtggccgg    2340
aggtgcccgg caccgaggtc ggcgccgacg cgtggatcgg cgccggcgcg gtggtccggg    2400
ccggcgtccg gatcgggcac ggcgcgatcg tcgcggccgg cgcggtcgtc acccgcgacg    2460
tcgccgacta cgagatcgtg gccggggtgc cggcccgccg gctgcggtcc cggttccccg    2520
acgacctggc cgaacggctg gtcgcgctgg cctggtggga ctggccgccg gggttcatca    2580
aggccaacat cgacctgttc cagcggccgc tgaccgccga caccctggcc gcgctggagg    2640
agcgggcccg cgccctgccc acaccccgg gtggtgccgc gtgaccgccg gtacgggcca    2700
gccggtcgtc gccgcgcccg gcagggcgct cgccgaccgg gtggtggtgg tgaccggcgc    2760
cagccgcggt gtcggccgcg acctcgcccg ggtgttcgcc gaccacggcg cccgcctcgg    2820
cctgctggcc cgcagccggg acgcgctcga cgacctcggc ggcacgctca ccgccgccgg    2880
tgccgacgtc ctcgccgtgc cgtgcgacgt cggcgaaccg gactcgctgg ccggcgcggt    2940
cgacgccgtc gccgggcact cggagggat cgactcggtc gtcgtcaacg ccggcatctc    3000
gcccgtcgcc cgtcgggcgc accacctgcc gatcgacgcc tggcacgacg tgctggcgac    3060
caacctgacc ggcgggttcg tcacggcgcg ggcggcgtat ccgcacctgg cccgctcggg    3120
gcgtggccgg ctggtgttca ccacctcggt catggccgcc accccgcggc gcgggctgag    3180
cgcgtacgcg cgtcgaagg ccggcctgga ggggctcacc cgggccctgg ccgctgactg    3240
ggcggggac ggaatcctgg tcaacgcggt cgcgccgggg ttcttcgaca ccgggctcgg    3300
cgccgccttc cacacctcgc agcgcctgca cgagcaggtc gtcggtcgta cgccggtggc    3360
ccggttcggc cgcgccgacg agttggccgc cgcgttcgtc ttcctggccg gtgacgcctg    3420
cggttacctg accggtcagg tgctcgccgt cgacggcggc tacggcctgg gctga         3475
```

<210> SEQ ID NO 2
<211> LENGTH: 828
<212> TYPE: DNA
<213> ORGANISM: Polymorphospora rubra K07-0510
<220> FEATURE:
<221> NAME/KEY: CDS
<222> LOCATION: (1)..(828)

<400> SEQUENCE: 2

```
gtg acc cga ccg gac gcc ccg ggc cca ccg gtc gcc gcc ccg gac ccg    48
Val Thr Arg Pro Asp Ala Pro Gly Pro Pro Val Ala Ala Pro Asp Pro
 1               5                  10                  15 gcc gac gcc gtc gtg acg gcc gtc gag ccg tac gtg gtc cgg gcg acg    96
Ala Asp Ala Val Val Thr Ala Val Glu Pro Tyr Val Val Arg Ala Thr
            20                  25                  30 atc aac cga ccg gcc cgc cgc aac gcc atc gac ctc gcc gtg atc gag   144
Ile Asn Arg Pro Ala Arg Arg Asn Ala Ile Asp Leu Ala Val Ile Glu
        35                  40                  45 ggc ctc gaa cgc gcc atc gac ctc gcc gag gcg acc ggc gcc cgg gtc   192
Gly Leu Glu Arg Ala Ile Asp Leu Ala Glu Ala Thr Gly Ala Arg Val
    50                  55                  60 ctg gtg ctg cgc ggc gcc ggc ggc acc ttc tgc tcc ggc gcc gac ctg   240
Leu Val Leu Arg Gly Ala Gly Gly Thr Phe Cys Ser Gly Ala Asp Leu
65                  70                  75                  80 cgc gtc ctg gag gag atg agc gtc gac ccg cac cgg gtg gag acg ttc   288
```

```
Arg Val Leu Glu Glu Met Ser Val Asp Pro His Arg Val Glu Thr Phe
                 85                  90                  95 atg gtg cgg ctc gcc ctc gtg ctg cgc cgg ctg gag acc gcc cgg ttc      336
Met Val Arg Leu Ala Leu Val Leu Arg Arg Leu Glu Thr Ala Arg Phe
            100                 105                 110 gtc tcg gtc gcg gtc gtg gag ggg cac gcc gtc gcg ggc ggc tgc gag      384
Val Ser Val Ala Val Val Glu Gly His Ala Val Ala Gly Gly Cys Glu
                115                 120                 125 atc ctg ctc gcc tgc gac gtc tcg gtc gcc gcc acc gac gcc cgc atc      432
Ile Leu Leu Ala Cys Asp Val Ser Val Ala Ala Thr Asp Ala Arg Ile
        130                 135                 140 ggc gac cgc cat ctc gag tac ggg ctg gtc ccc gcc gcc ggc ggc tcg      480
Gly Asp Arg His Leu Glu Tyr Gly Leu Val Pro Ala Ala Gly Gly Ser
145                 150                 155                 160 gta cgg ctg gcc cgc acc ctg ccc aag gcc cgg ggc aac tac ctg ctg      528
Val Arg Leu Ala Arg Thr Leu Pro Lys Ala Arg Gly Asn Tyr Leu Leu
                165                 170                 175 ctc gcc gcc gac ctg ctc acc ggg gag cag gcg gcg cag tgg gga ctg      576
Leu Ala Ala Asp Leu Leu Thr Gly Glu Gln Ala Ala Gln Trp Gly Leu
            180                 185                 190 gtc agc gtc gcg gtg ccg cca acc gac ctg gaa ccc cgg gtg gac gcc      624
Val Ser Val Ala Val Pro Pro Thr Asp Leu Glu Pro Arg Val Asp Ala
                195                 200                 205 ctg gtc ggg cgg ctc gtc ggc cac agc gcc gac gcg ctc gcc gtg gtc      672
Leu Val Gly Arg Leu Val Gly His Ser Ala Asp Ala Leu Ala Val Val
        210                 215                 220 aag aag atg gtc tgg acc gcc gac cac gaa ccc cgg ccg gac gcc atg      720
Lys Lys Met Val Trp Thr Ala Asp His Glu Pro Arg Pro Asp Ala Met
225                 230                 235                 240 tcc tgg gaa cgc cgg ctc ttc ctg cgc cac ctc ggc tcc gaa gac gtg      768
Ser Trp Glu Arg Arg Leu Phe Leu Arg His Leu Gly Ser Glu Asp Val
                245                 250                 255 tcc gag ggg ctg cgc gcc ttc cgc gag cgg cgc cgg ccg gcg ttc cgc      816
Ser Glu Gly Leu Arg Ala Phe Arg Glu Arg Arg Arg Pro Ala Phe Arg
            260                 265                 270 gcc gat gac tga                                                      828
Ala Asp Asp
        275

<210> SEQ ID NO 3
<211> LENGTH: 275
<212> TYPE: PRT
<213> ORGANISM: Polymorphospora rubra K07-0510

<400> SEQUENCE: 3

Val Thr Arg Pro Asp Ala Pro Gly Pro Pro Val Ala Ala Pro Asp Pro
1               5                   10                  15

Ala Asp Ala Val Val Thr Ala Val Glu Pro Tyr Val Val Arg Ala Thr
                20                  25                  30

Ile Asn Arg Pro Ala Arg Arg Asn Ala Ile Asp Leu Ala Val Ile Glu
            35                  40                  45

Gly Leu Glu Arg Ala Ile Asp Leu Ala Glu Ala Thr Gly Ala Arg Val
        50                  55                  60

Leu Val Leu Arg Gly Ala Gly Gly Thr Phe Cys Ser Gly Ala Asp Leu
65                  70                  75                  80

Arg Val Leu Glu Glu Met Ser Val Asp Pro His Arg Val Glu Thr Phe
                85                  90                  95

Met Val Arg Leu Ala Leu Val Leu Arg Arg Leu Glu Thr Ala Arg Phe
            100                 105                 110
```

```
Val Ser Val Ala Val Glu Gly His Ala Val Ala Gly Gly Cys Glu
        115                 120                 125

Ile Leu Leu Ala Cys Asp Val Ser Val Ala Ala Thr Asp Ala Arg Ile
130                 135                 140

Gly Asp Arg His Leu Glu Tyr Gly Leu Val Pro Ala Ala Gly Gly Ser
145                 150                 155                 160

Val Arg Leu Ala Arg Thr Leu Pro Lys Ala Arg Gly Asn Tyr Leu Leu
                165                 170                 175

Leu Ala Ala Asp Leu Leu Thr Gly Glu Gln Ala Ala Gln Trp Gly Leu
            180                 185                 190

Val Ser Val Ala Val Pro Pro Thr Asp Leu Glu Pro Arg Val Asp Ala
        195                 200                 205

Leu Val Gly Arg Leu Val Gly His Ser Ala Asp Ala Leu Ala Val Val
    210                 215                 220

Lys Lys Met Val Trp Thr Ala Asp His Glu Pro Arg Pro Asp Ala Met
225                 230                 235                 240

Ser Trp Glu Arg Arg Leu Phe Leu Arg His Leu Gly Ser Glu Asp Val
                245                 250                 255

Ser Glu Gly Leu Arg Ala Phe Arg Glu Arg Arg Pro Ala Phe Arg
            260                 265                 270

Ala Asp Asp
        275

<210> SEQ ID NO 4
<211> LENGTH: 1026
<212> TYPE: DNA
<213> ORGANISM: Polymorphospora rubra K07-0510
<220> FEATURE:
<221> NAME/KEY: CDS
<222> LOCATION: (1)..(1026)

<400> SEQUENCE: 4 atg tcg acc tcg acg gtg atc gga aca ggt tcg tac cta ccc cgc cgc        48
Met Ser Thr Ser Thr Val Ile Gly Thr Gly Ser Tyr Leu Pro Arg Arg
1               5                   10                  15 gtc ctc agc agc ggc gaa ctg gcc cgc cgg gtc ggt gtg gcg gag aac        96
Val Leu Ser Ser Gly Glu Leu Ala Arg Arg Val Gly Val Ala Glu Asn
            20                  25                  30 tgg atc gtg gag aag acc ggg atc cgg gaa cgc cgg gtg gcc gcc gac       144
Trp Ile Val Glu Lys Thr Gly Ile Arg Glu Arg Arg Val Ala Ala Asp
        35                  40                  45 gag gag gcc acc tcc gac ctg gcc acc cgg gcc gcg cgc cgg gcg ctg       192
Glu Glu Ala Thr Ser Asp Leu Ala Thr Arg Ala Ala Arg Arg Ala Leu
    50                  55                  60 cgg acc gcc cgg ctg gac ccg gcc gac gtc gac ctg atc gtg ctg gcg       240
Arg Thr Ala Arg Leu Asp Pro Ala Asp Val Asp Leu Ile Val Leu Ala
65                  70                  75                  80 acc tcc aca ccg gac cgg ccg atg ccg gcc acc gcc agc acc gtg cag       288
Thr Ser Thr Pro Asp Arg Pro Met Pro Ala Thr Ala Ser Thr Val Gln
                85                  90                  95 gcc aac ctc ggc gcc cgc cag gcg gtc gcg ttc gac gtc gac gcg gtg       336
Ala Asn Leu Gly Ala Arg Gln Ala Val Ala Phe Asp Val Asp Ala Val
            100                 105                 110 tgc agc ggc ttc gtg tac gcc ctc gtc gtc gcc cac tcg atg ctg aac       384
Cys Ser Gly Phe Val Tyr Ala Leu Val Val Ala His Ser Met Leu Asn
        115                 120                 125 agc gag ggc tgg gcc cgt acc gcg ctg gtg atc ggc gcc gac acg tac       432
Ser Glu Gly Trp Ala Arg Thr Ala Leu Val Ile Gly Ala Asp Thr Tyr
```

|  |  |  |  |  |  |  |  |  |  |  |  |  |  |  |  |  |
|---|---|---|---|---|---|---|---|---|---|---|---|---|---|---|---|---|
|  |  | 130 |  |  |  | 135 |  |  |  | 140 |  |  |  |  |  |  |

```
tcg cgg gtc ctg gac tac acc gac cgg cgt acc gcg gtg ctc ttc ggc      480
Ser Arg Val Leu Asp Tyr Thr Asp Arg Arg Thr Ala Val Leu Phe Gly
145                 150                 155                 160 gac ggt gcc ggc gcg gtc gtc ctc ggc cgg gag acc ggc ggg agc          528
Asp Gly Ala Gly Ala Val Val Leu Gly Arg Glu Thr Gly Gly Gly Ser
                165                 170                 175 gga atc cgg gcc acc acc ctg ggc acc gac ggc acc ctc gcc gac ctc      576
Gly Ile Arg Ala Thr Thr Leu Gly Thr Asp Gly Thr Leu Ala Asp Leu
            180                 185                 190 gtc cag atc ccg gcc ggc ggc agc cgc cgg ccg gcg agc gcg cag acg      624
Val Gln Ile Pro Ala Gly Gly Ser Arg Arg Pro Ala Ser Ala Gln Thr
        195                 200                 205 gtc gag gcc ggc gac cac tac ttc gcg atg cgc ggc ggc gac gtc cgc      672
Val Glu Ala Gly Asp His Tyr Phe Ala Met Arg Gly Gly Asp Val Arg
    210                 215                 220 agg ctg gcc aac cag gtc ttc ccg gca ctg gtc ggg caa ctg ctc aag      720
Arg Leu Ala Asn Gln Val Phe Pro Ala Leu Val Gly Gln Leu Leu Lys
225                 230                 235                 240 gcg gcc tcg ctc gac ctg gac cag gtc gac ctg atc gcc gcc cac cag      768
Ala Ala Ser Leu Asp Leu Asp Gln Val Asp Leu Ile Ala Ala His Gln
                245                 250                 255 gcc aac ggc acg atg ctc acc gac tgg tcg cgg gac ctc ggc ctg cgc      816
Ala Asn Gly Thr Met Leu Thr Asp Trp Ser Arg Asp Leu Gly Leu Arg
            260                 265                 270 ccg ggg gtg ctg cac cgc acc gtc gag cgg tac ggc aac acc ggt gcc      864
Pro Gly Val Leu His Arg Thr Val Glu Arg Tyr Gly Asn Thr Gly Ala
        275                 280                 285 gcc tcg gtc ccg gtc acc ctc gac gac gcc gta cgc acc ggg cgg ctc      912
Ala Ser Val Pro Val Thr Leu Asp Asp Ala Val Arg Thr Gly Arg Leu
    290                 295                 300 ggt gcc gcc gcc acc ctg ctg atg gtc gcc ttc ggc ggc ggg atg acc      960
Gly Ala Ala Ala Thr Leu Leu Met Val Ala Phe Gly Gly Gly Met Thr
305                 310                 315                 320 tgg ggc ggc gtc gcc ctg gac tgg tcc gcc gac ccg tcg gtt ccc cgc     1008
Trp Gly Gly Val Ala Leu Asp Trp Ser Ala Asp Pro Ser Val Pro Arg
                325                 330                 335 tcc aac tgc gtg agg tga                                            1026
Ser Asn Cys Val Arg
            340
```

<210> SEQ ID NO 5
<211> LENGTH: 341
<212> TYPE: PRT
<213> ORGANISM: Polymorphospora rubra K07-0510

<400> SEQUENCE: 5

Met Ser Thr Ser Thr Val Ile Gly Thr Gly Ser Tyr Leu Pro Arg Arg
1               5                   10                  15

Val Leu Ser Ser Gly Glu Leu Ala Arg Arg Val Gly Val Ala Glu Asn
            20                  25                  30

Trp Ile Val Glu Lys Thr Gly Ile Arg Glu Arg Val Ala Ala Asp
        35                  40                  45

Glu Glu Ala Thr Ser Asp Leu Ala Thr Arg Ala Ala Arg Arg Ala Leu
    50                  55                  60

Arg Thr Ala Arg Leu Asp Pro Ala Asp Val Asp Leu Ile Val Leu Ala
65                  70                  75                  80

Thr Ser Thr Pro Asp Arg Pro Met Pro Ala Thr Ala Ser Thr Val Gln
                85                  90                  95

```
Ala Asn Leu Gly Ala Arg Gln Ala Val Ala Phe Asp Val Asp Ala Val
                100                 105                 110

Cys Ser Gly Phe Val Tyr Ala Leu Val Val Ala His Ser Met Leu Asn
            115                 120                 125

Ser Glu Gly Trp Ala Arg Thr Ala Leu Val Ile Gly Ala Asp Thr Tyr
        130                 135                 140

Ser Arg Val Leu Asp Tyr Thr Asp Arg Arg Thr Ala Val Leu Phe Gly
145                 150                 155                 160

Asp Gly Ala Gly Ala Val Val Leu Gly Arg Glu Thr Gly Gly Gly Ser
                165                 170                 175

Gly Ile Arg Ala Thr Thr Leu Gly Thr Asp Gly Thr Leu Ala Asp Leu
            180                 185                 190

Val Gln Ile Pro Ala Gly Gly Ser Arg Arg Pro Ala Ser Ala Gln Thr
        195                 200                 205

Val Glu Ala Gly Asp His Tyr Phe Ala Met Arg Gly Gly Asp Val Arg
                210                 215                 220

Arg Leu Ala Asn Gln Val Phe Pro Ala Leu Val Gly Gln Leu Leu Lys
225                 230                 235                 240

Ala Ala Ser Leu Asp Leu Asp Gln Val Asp Leu Ile Ala Ala His Gln
                245                 250                 255

Ala Asn Gly Thr Met Leu Thr Asp Trp Ser Arg Asp Leu Gly Leu Arg
            260                 265                 270

Pro Gly Val Leu His Arg Thr Val Glu Arg Tyr Gly Asn Thr Gly Ala
        275                 280                 285

Ala Ser Val Pro Val Thr Leu Asp Asp Ala Val Arg Thr Gly Arg Leu
                290                 295                 300

Gly Ala Ala Ala Thr Leu Leu Met Val Ala Phe Gly Gly Gly Met Thr
305                 310                 315                 320

Trp Gly Gly Val Ala Leu Asp Trp Ser Ala Asp Pro Ser Val Pro Arg
                325                 330                 335

Ser Asn Cys Val Arg
            340

<210> SEQ ID NO 6
<211> LENGTH: 780
<212> TYPE: DNA
<213> ORGANISM: Polymorphospora rubra K07-0510
<220> FEATURE:
<221> NAME/KEY: CDS
<222> LOCATION: (1)..(780)

<400> SEQUENCE: 6 atg acc acg tcc gca ctc ggc gcc gaa ccg ggc gcc acc gat ccg ccg    48
Met Thr Thr Ser Ala Leu Gly Ala Glu Pro Gly Ala Thr Asp Pro Pro
1               5                   10                  15 gcc gcc ccg ccg gtc tcc tac gcc ccg tcc ggc cgg atg ccc cgg acg    96
Ala Ala Pro Pro Val Ser Tyr Ala Pro Ser Gly Arg Met Pro Arg Thr
                20                  25                  30 atc aac cgc tgg ccg cgc ccg ttc gcg ccg cgc aac atc ctc ggc gtg   144
Ile Asn Arg Trp Pro Arg Pro Phe Ala Pro Arg Asn Ile Leu Gly Val
            35                  40                  45 ctg cgg gcc cgg ctg cgc ggc gcc acg atc agc ctc aac cag gtc aag   192
Leu Arg Ala Arg Leu Arg Gly Ala Thr Ile Ser Leu Asn Gln Val Lys
        50                  55                  60 ttc gac gag tcc acc gcg gag cgc aac gcg ctg gtg atg gaa cac gcg   240
Phe Asp Glu Ser Thr Ala Glu Arg Asn Ala Leu Val Met Glu His Ala
65                  70                  75                  80
```

```
ctg ctg cgg cac agc cac gtc gcc cgg tac gcg atc gtc ggc ccg ttc    288
Leu Leu Arg His Ser His Val Ala Arg Tyr Ala Ile Val Gly Pro Phe
            85                  90                  95 acc tcg ctg ttc aag gtc cgg gtc ggc ccg tac gcg ggg atc gcc gag    336
Thr Ser Leu Phe Lys Val Arg Val Gly Pro Tyr Ala Gly Ile Ala Glu
                100                 105                 110 aag gtg acc gtc ggt gcc ctg ccg cac tgg ccg gaa ctg ccg acc agt    384
Lys Val Thr Val Gly Ala Leu Pro His Trp Pro Glu Leu Pro Thr Ser
            115                 120                 125 cac gtc ttc ccg gtc aac gcc gag ttc ggc ttc tgc gcg ggg gag tgg    432
His Val Phe Pro Val Asn Ala Glu Phe Gly Phe Cys Ala Gly Glu Trp
        130                 135                 140 ccg gag gtg ccc ggc acc gag gtc ggc gcc gac gcg tgg atc ggc gcc    480
Pro Glu Val Pro Gly Thr Glu Val Gly Ala Asp Ala Trp Ile Gly Ala
145                 150                 155                 160 ggc gcg gtg gtc cgg gcc ggc gtc cgg atc ggg cac ggc gcg atc gtc    528
Gly Ala Val Val Arg Ala Gly Val Arg Ile Gly His Gly Ala Ile Val
                165                 170                 175 gcg gcc ggc gcg gtc gtc acc cgc gac gtc gcc gac tac gag atc gtg    576
Ala Ala Gly Ala Val Val Thr Arg Asp Val Ala Asp Tyr Glu Ile Val
            180                 185                 190 gcc ggg gtg ccg gcc cgc cgg ctg cgg tcc cgg ttc ccc gac gac ctg    624
Ala Gly Val Pro Ala Arg Arg Leu Arg Ser Arg Phe Pro Asp Asp Leu
        195                 200                 205 gcc gaa cgg ctg gtc gcg ctg gcc tgg tgg gac tgg ccg ccg ggg ttc    672
Ala Glu Arg Leu Val Ala Leu Ala Trp Trp Asp Trp Pro Pro Gly Phe
    210                 215                 220 atc aag gcc aac atc gac ctg ttc cag cgg ccg ctg acc gcc gac acc    720
Ile Lys Ala Asn Ile Asp Leu Phe Gln Arg Pro Leu Thr Ala Asp Thr
225                 230                 235                 240 ctg gcc gcg ctg gag gag cgg gcc cgc gcc ctg ccc aca ccc ccg ggt    768
Leu Ala Ala Leu Glu Glu Arg Ala Arg Ala Leu Pro Thr Pro Pro Gly
                245                 250                 255 ggt gcc gcg tga                                                    780
Gly Ala Ala <210> SEQ ID NO 7
<211> LENGTH: 259
<212> TYPE: PRT
<213> ORGANISM: Polymorphospora rubra K07-0510

<400> SEQUENCE: 7

Met Thr Thr Ser Ala Leu Gly Ala Glu Pro Gly Ala Thr Asp Pro Pro
1               5                   10                  15

Ala Ala Pro Pro Val Ser Tyr Ala Pro Ser Gly Arg Met Pro Arg Thr
                20                  25                  30

Ile Asn Arg Trp Pro Arg Pro Phe Ala Pro Arg Asn Ile Leu Gly Val
            35                  40                  45

Leu Arg Ala Arg Leu Arg Gly Ala Thr Ile Ser Leu Asn Gln Val Lys
        50                  55                  60

Phe Asp Glu Ser Thr Ala Glu Arg Asn Ala Leu Val Met Glu His Ala
65                  70                  75                  80

Leu Leu Arg His Ser His Val Ala Arg Tyr Ala Ile Val Gly Pro Phe
                85                  90                  95

Thr Ser Leu Phe Lys Val Arg Val Gly Pro Tyr Ala Gly Ile Ala Glu
            100                 105                 110

Lys Val Thr Val Gly Ala Leu Pro His Trp Pro Glu Leu Pro Thr Ser
        115                 120                 125
```

```
His Val Phe Pro Val Asn Ala Glu Phe Gly Phe Cys Ala Gly Glu Trp
    130                 135                 140

Pro Glu Val Pro Gly Thr Glu Val Gly Ala Asp Ala Trp Ile Gly Ala
145                 150                 155                 160

Gly Ala Val Val Arg Ala Gly Val Arg Ile Gly His Gly Ala Ile Val
                165                 170                 175

Ala Ala Gly Ala Val Val Thr Arg Asp Val Ala Asp Tyr Glu Ile Val
            180                 185                 190

Ala Gly Val Pro Ala Arg Arg Leu Arg Ser Arg Phe Pro Asp Asp Leu
        195                 200                 205

Ala Glu Arg Leu Val Ala Leu Ala Trp Trp Asp Trp Pro Pro Gly Phe
    210                 215                 220

Ile Lys Ala Asn Ile Asp Leu Phe Gln Arg Pro Leu Thr Ala Asp Thr
225                 230                 235                 240

Leu Ala Ala Leu Glu Glu Arg Ala Arg Ala Leu Pro Thr Pro Pro Gly
                245                 250                 255

Gly Ala Ala

<210> SEQ ID NO 8
<211> LENGTH: 795
<212> TYPE: DNA
<213> ORGANISM: Polymorphospora rubra K07-0510
<220> FEATURE:
<221> NAME/KEY: CDS
<222> LOCATION: (1)..(795)

<400> SEQUENCE: 8 gtg acc gcc ggt acg ggc cag ccg gtc gtc gcc gcg ccc ggc agg gcg      48
Val Thr Ala Gly Thr Gly Gln Pro Val Val Ala Ala Pro Gly Arg Ala
1               5                   10                  15 ctc gcc gac cgg gtg gtg gtg gtg acc ggc gcc agc cgc ggt gtc ggc      96
Leu Ala Asp Arg Val Val Val Val Thr Gly Ala Ser Arg Gly Val Gly
            20                  25                  30 cgc gac ctc gcc cgg gtg ttc gcc gac cac ggc gcc cgc ctc ggc ctg     144
Arg Asp Leu Ala Arg Val Phe Ala Asp His Gly Ala Arg Leu Gly Leu
        35                  40                  45 ctg gcc cgc agc cgg gac gcg ctc gac gac ctc ggc ggc acg ctc acc     192
Leu Ala Arg Ser Arg Asp Ala Leu Asp Asp Leu Gly Gly Thr Leu Thr
    50                  55                  60 gcc gcc ggt gcc gac gtc ctc gcc gtg ccg tgc gac gtc ggc gaa ccg     240
Ala Ala Gly Ala Asp Val Leu Ala Val Pro Cys Asp Val Gly Glu Pro
65                  70                  75                  80 gac tcg ctg gcc ggc gcg gtc gac gcc gtc gcc ggg cac ttc gga ggg     288
Asp Ser Leu Ala Gly Ala Val Asp Ala Val Ala Gly His Phe Gly Gly
                85                  90                  95 atc gac tcg gtc gtc gtc aac gcc ggc atc tcg ccc gtc gcc cgt cgg     336
Ile Asp Ser Val Val Val Asn Ala Gly Ile Ser Pro Val Ala Arg Arg
            100                 105                 110 gcg cac cac ctg ccg atc gac gcc tgg cac gac gtg ctg gcg acc aac     384
Ala His His Leu Pro Ile Asp Ala Trp His Asp Val Leu Ala Thr Asn
        115                 120                 125 ctg acc ggc ggg ttc gtc acg gcg cgg gcg gcg tat ccg cac ctg gcc     432
Leu Thr Gly Gly Phe Val Thr Ala Arg Ala Ala Tyr Pro His Leu Ala
    130                 135                 140 cgc tcg ggg cgt ggc cgg ctg gtg ttc acc acc tcg gtc atg gcc gcc     480
Arg Ser Gly Arg Gly Arg Leu Val Phe Thr Thr Ser Val Met Ala Ala
145                 150                 155                 160 acc ccg cgg cgc ggg ctg agc gcg tac gcg gcg tcg aag gcc ggc ctg     528
Thr Pro Arg Arg Gly Leu Ser Ala Tyr Ala Ala Ser Lys Ala Gly Leu
```

```
                Thr Pro Arg Arg Gly Leu Ser Ala Tyr Ala Ala Ser Lys Ala Gly Leu
                            165                 170                 175 gag ggg ctc acc cgg gcc ctg gcc gct gac tgg gcg ggg gac gga atc          576
Glu Gly Leu Thr Arg Ala Leu Ala Ala Asp Trp Ala Gly Asp Gly Ile
            180                 185                 190 ctg gtc aac gcg gtc gcg ccg ggg ttc ttc gac acc ggg ctc ggc gcc          624
Leu Val Asn Ala Val Ala Pro Gly Phe Phe Asp Thr Gly Leu Gly Ala
        195                 200                 205 gcc ttc cac acc tcg cag cgc ctg cac gag cag gtc gtc ggt cgt acg          672
Ala Phe His Thr Ser Gln Arg Leu His Glu Gln Val Val Gly Arg Thr
    210                 215                 220 ccg gtg gcc cgg ttc ggc cgc gcc gac gag ttg gcc gcc gcg ttc gtc          720
Pro Val Ala Arg Phe Gly Arg Ala Asp Glu Leu Ala Ala Ala Phe Val
225                 230                 235                 240 ttc ctg gcc ggt gac gcc tgc ggt tac ctg acc ggt cag gtg ctc gcc          768
Phe Leu Ala Gly Asp Ala Cys Gly Tyr Leu Thr Gly Gln Val Leu Ala
                245                 250                 255 gtc gac ggc ggc tac ggc ctg ggc tga                                      795
Val Asp Gly Gly Tyr Gly Leu Gly
                260

<210> SEQ ID NO 9
<211> LENGTH: 264
<212> TYPE: PRT
<213> ORGANISM: Polymorphospora rubra K07-0510

<400> SEQUENCE: 9

Val Thr Ala Gly Thr Gly Gln Pro Val Ala Ala Pro Gly Arg Ala
1               5                   10                  15

Leu Ala Asp Arg Val Val Val Thr Gly Ala Ser Arg Gly Val Gly
                20                  25                  30

Arg Asp Leu Ala Arg Val Phe Ala Asp His Gly Ala Arg Leu Gly Leu
            35                  40                  45

Leu Ala Arg Ser Arg Asp Ala Leu Asp Asp Leu Gly Gly Thr Leu Thr
        50                  55                  60

Ala Ala Gly Ala Asp Val Leu Ala Val Pro Cys Asp Val Gly Glu Pro
65                  70                  75                  80

Asp Ser Leu Ala Gly Ala Val Asp Ala Val Ala Gly His Phe Gly Gly
                85                  90                  95

Ile Asp Ser Val Val Val Asn Ala Gly Ile Ser Pro Val Ala Arg Arg
                100                 105                 110

Ala His His Leu Pro Ile Asp Ala Trp His Asp Val Leu Ala Thr Asn
            115                 120                 125

Leu Thr Gly Gly Phe Val Thr Ala Arg Ala Ala Tyr Pro His Leu Ala
        130                 135                 140

Arg Ser Gly Arg Gly Arg Leu Val Phe Thr Thr Ser Val Met Ala Ala
145                 150                 155                 160

Thr Pro Arg Arg Gly Leu Ser Ala Tyr Ala Ala Ser Lys Ala Gly Leu
                165                 170                 175

Glu Gly Leu Thr Arg Ala Leu Ala Ala Asp Trp Ala Gly Asp Gly Ile
            180                 185                 190

Leu Val Asn Ala Val Ala Pro Gly Phe Phe Asp Thr Gly Leu Gly Ala
        195                 200                 205

Ala Phe His Thr Ser Gln Arg Leu His Glu Gln Val Val Gly Arg Thr
    210                 215                 220

Pro Val Ala Arg Phe Gly Arg Ala Asp Glu Leu Ala Ala Ala Phe Val
225                 230                 235                 240
```

Phe Leu Ala Gly Asp Ala Cys Gly Tyr Leu Thr Gly Gln Val Leu Ala
            245                 250                 255

Val Asp Gly Gly Tyr Gly Leu Gly
            260

<210> SEQ ID NO 10
<211> LENGTH: 37
<212> TYPE: DNA
<213> ORGANISM: Artificial Sequence
<220> FEATURE:
<223> OTHER INFORMATION: primer

<400> SEQUENCE: 10
aaagggctgc agaggaggcg taccgtgacc cgaccgg                              37

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
aaagggaggc ctgctcagcc caggccgtag                                      30

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
aaagggcata tgtcgacctc gacggtg                                         27

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
aaagggctcg agtcacctca cgcagttgga                                      30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
aaagggcata tggtgaccgc cggtacgggc                                      30

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
aaagggctcg agtcagccca ggccgtagcc                                      30

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
aaagggcata tggtgacccg accggacgcc                                    30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17 aaaggggat cctcagtcat cggcgcggaa                                     30

<210> SEQ ID NO 18
<211> LENGTH: 1946
<212> TYPE: DNA
<213> ORGANISM: Artificial Sequence
<220> FEATURE:
<223> OTHER INFORMATION: orf AB for Corynebacterium

<400> SEQUENCE: 18
atgtccgttt cccgcgttgt tggctccgct gctacccgca ccgttacccg cccagacgct 60
ccaggcccac cagttgctgc tccagaccca gctgacgctg ttgttaccgc tgttgagcca 120
tacgttgttc gcgctaccat caaccgccca gctcgccgca acgctatcga cctggctgtt 180
atcgagggcc tggagcgcgc tatcgacctg gctgaggcta ccggcgctcg cgttctggtt 240
ctgcgcggcg ctggcggcac cttctgctcc ggcgctgacc tgcgcgttct ggaggagatg 300
tccgttgacc cacaccgcgt tgagaccttc atggttcgcc tggctctggt tctgcgccgc 360
ctggagaccg ctcgcttcgt ttccgttgct gttgttgagg gccacgctgt tgctggcggc 420
tgcgagatcc tgctggcttg cgacgtttcc gttgctgcta ccgacgctcg catcggcgac 480
cgccacctgg agtacggcct ggttccagct gctggcggct ccgttcgcct ggctcgcacc 540
ctgccaaagg ctcgcggcaa ctacctgctg ctggctgctg acctgctgac cggcgagcag 600
gctgctcagt ggggcctggt ttccgttgct gttccaccaa ccgacctgga gccacgcgtt 660
gacgctctgg ttggccgcct ggttggccac tccgctgacg ctctggctgt tgttaagaag 720
atggtttgga ccgctgacca cgagccacgc ccagacgcta tgtcctggga gcgccgcctg 780
ttcctgcgcc acctgggctc cgaggacgtt tccgagggcc tgcgcgcttt ccgcgagcgc 840
cgccgcccag ctttccgcgc tgacgactaa ctccgtacgg ccgcccgacc ggacggcccg 900
accgcaagga gaccacatgt ccacctccac cgttatcggc accggctcct acctgccacg 960
ccgcgttctg tcctccggcg agctggctcg ccgcgttggc gttgctgaga actggatcgt 1020
tgagaagacc ggcatccgcg agcgccgcgt tgctgctgac gaggaggcta cctccgacct 1080
ggctacccgc gctgctcgcc gcgctctgcg caccgctcgc ctggacccag ctgacgttga 1140
cctgatcgtt ctggctacct ccaccccaga ccgcccaatg ccagctaccg cttccaccgt 1200
tcaggctaac ctgggcgctc gccaggctgt tgctttcgac gttgacgctg tttgctccgg 1260
cttcgtttac gctctggttg ttgctcactc catgctgaac tccgagggct gggctcgcac 1320
cgctctggtt atcggcgctg acacctactc ccgcgttctg gactacaccg accgccgcac 1380

-continued

```
cgctgttctg ttcggcgacg gcgctggcgc tgttgttctg ggccgcgaga ccggcggcgg    1440
ctccggcatc cgcgctacca ccctgggcac cgacggcacc ctggctgacc tggttcagat    1500
cccagctggc ggctcccgcc gcccagcttc cgctcagacc gttgaggctg cgaccacta     1560 cttcgctatg cgcggcggcg acgttcgccg cctggctaac caggttttcc cagctctggt    1620
tggccagctg ctgaaggctg cttccctgga cctggaccag gttgacctga tcgctgctca    1680
ccaggctaac ggcaccatgc tgaccgactg gtcccgcgac ctgggcctgc gccaggcgt     1740 tctgcaccgc accgttgagc gctacggcaa caccggcgct gcttccgttc agttaccct     1800 ggacgacgct gttcgcaccg gccgcctggg cgctgctgct accctgctga tggttgcttt    1860
cggcggcggc atgacctggg cggcgttgc tctggactgg tccgctgacc catccgttcc     1920
acgctccaac tgcgttcgct aaagtg                                         1946
```

<210> SEQ ID NO 19
<211> LENGTH: 1571
<212> TYPE: DNA
<213> ORGANISM: Artificial Sequence
<220> FEATURE:
<223> OTHER INFORMATION: orfCD for Corynebacterium

<400> SEQUENCE: 19

```
atgaccacct ccgctctggg cgctgagcca ggcgctaccg acccaccagc tgctccacca     60
gtttcctacg ctccatccgg ccgcatgcca cgcaccatca accgctggcc acgcccattc    120
gctccacgca acatcctggg cgttctgcgc gctcgcctgc gcggcgctac catctccctg    180
aaccaggtta agttcgacga gtccaccgct gagcgcaacg ctctggttat ggagcacgct    240
ctgctgcgcc actcccacgt tgctcgctac gctatcgttg cccattcac ctccctgttc     300 aaggttcgcg ttggcccata cgctggcatc gctgagaagg ttaccgttgg cgctctgcca    360
cactggccag agctgccaac ctcccacgtt ttcccagtta acgctgagtt cggcttctgc    420
gctggcgagt ggccagaggt tccaggcacc gaggttggcg ctgacgcttg gatcggcgct    480
ggcgctgttg ttcgcgctgg cgttcgcatc ggccacggcg ctatcgttgc tgctggcgct    540
gttgttaccc gcgacgttgc tgactacgag atcgttgctg cgttccagc tcgccgcctg     600 cgctcccgct tcccagacga cctggctgag cgcctggttg ctctggcttg gtgggactgg    660
ccaccaggct tcatcaaggc taacatcgac ctgttccagc gcccactgac cgctgacacc    720
ctggctgctc tggaggagcg cgctcgcgct ctgccaaccc caccaggcgg cgctgcgtga    780
ccgctggcac cggccagcca gttgttgctg ctccaggccg cgctctggct gaccgcgttg    840
ttgttgttac cggcgcttcc cgcggcgttg gccgcgacct ggctcgcgtt tcgctgacc    900 acggcgctcg cctgggcctg ctggctcgct cccgcgacgc tctggacgac ctgggcggca    960
ccctgaccgc tgctggcgct gacgttctgg ctgttccatg cgacgttggc gagccagact   1020
ccctggctgg cgctgttgac gctgttgctg gccacttcgg cggcatcgac tccgttgttg   1080
ttaacgctgg catctcccca gttgctcgcc gcgctcacca cctgccaatc gacgcttggc   1140
acgacgttct ggctaccaac ctgaccggcg gcttcgttac cgctcgcgct gcttacccac   1200
acctggctcc tccggccgc ggcgcctgg ttttcaccac ctccgttatg gctgctaccc     1260
cacgccgcgg cctgtccgct tacgctgctt ccaaggctgg cctggagggc ctgacccgcg   1320
ctctggctgc tgactgggct ggcgacggca tcctggttaa cgctgttgct ccaggcttct   1380
tcgacaccgg cctgggcgct gctttccaca cctcccagcg cctgcacgag caggttgttg   1440
```

```
gccgcacccc agttgctcgc ttcggccgcg ctgacgagct ggctgctgct ttcgttttcc    1500
tggctggcga cgcttgcggc tacctgaccg gccaggttct ggctgttgac ggcggctacg    1560
gcctgggcta a                                                          1571

<210> SEQ ID NO 20
<211> LENGTH: 39
<212> TYPE: DNA
<213> ORGANISM: Artificial Sequence
<220> FEATURE:
<223> OTHER INFORMATION: primer

<400> SEQUENCE: 20
agaggagaca caacgagctc atgtccgttt cccgcgttg                            39

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
agcggaggtg gtcatcactt tagcgaacgc agttg                                35

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
atgaccacct ccgctctg                                                   18

<210> SEQ ID NO 23
<211> LENGTH: 38
<212> TYPE: DNA
<213> ORGANISM: Artificial Sequence
<220> FEATURE:
<223> OTHER INFORMATION: primer

<400> SEQUENCE: 23
ccgatatcct gcaggagctc ttagcccagg ccgtagcc                             38
```